US012295975B2

(12) United States Patent
Grasset et al.

(10) Patent No.: US 12,295,975 B2
(45) Date of Patent: May 13, 2025

(54) SEROTONIN PRODUCING BACTERIA

(71) Applicant: BIOGAIA AB, Stockholm (SE)

(72) Inventors: Estelle Grasset, Les Achards (FR); Muhammed Khan, Mölndal (SE); Bo Möllstam, Lerum (SE); Stefan Roos, Uppsala (SE)

(73) Assignee: BIOGAIA AB, Stockholm (SE)

( * ) Notice: Subject to any disclaimer, the term of this patent is extended or adjusted under 35 U.S.C. 154(b) by 251 days.

(21) Appl. No.: 17/623,543

(22) PCT Filed: Nov. 6, 2020

(86) PCT No.: PCT/SE2020/051075
§ 371 (c)(1),
(2) Date: Dec. 28, 2021

(87) PCT Pub. No.: WO2021/091474
PCT Pub. Date: May 14, 2021

(65) Prior Publication Data
US 2022/0354909 A1 Nov. 10, 2022

(30) Foreign Application Priority Data
Nov. 8, 2019 (SE) .................... 1951292-0

(51) Int. Cl.
A61K 35/747 (2015.01)
A61P 25/00 (2006.01)
A61P 25/28 (2006.01)
C12N 1/20 (2006.01)
C12Q 1/02 (2006.01)
C12R 1/225 (2006.01)

(52) U.S. Cl.
CPC ............ A61K 35/747 (2013.01); A61P 25/00 (2018.01); C12N 1/205 (2021.05); C12Q 1/02 (2013.01); C12R 2001/225 (2021.05)

(58) Field of Classification Search
CPC .................................................. A61K 35/747
See application file for complete search history.

(56) References Cited

U.S. PATENT DOCUMENTS

2019/0112675 A1  4/2019  Ma et al.

FOREIGN PATENT DOCUMENTS

| CA | 3089187 A1 | 8/2019 | |
| EP | 0753303 A2 | 1/1997 | |
| EP | 3747988 A1 | 12/2020 | |
| WO | 2006110088 A1 | 10/2006 | |
| WO | WO-2017212433 A1 * | 12/2017 | ........... A61K 35/745 |
| WO | 2019151843 A1 | 8/2019 | |

OTHER PUBLICATIONS

International Seach Report and Written Opinion corresponding to International application No. PCT/SE2020/051075, Jan. 26, 2021, 11 pages.
Nakaita et al. "Heat-Killed Lactobacillus brevis SBC8803 Induces Serotonin Release from Intestinal Cells" Food and Nutrition Sciences, (2013) 04(08):767-771.
Sara Bover Cid et al. "Amino acid decarboxylation by Lactobacillus curvatus CTC273 affected by the pH and glucose availability." Food Microbiology 25, pp. 269-277 (2008).
Visuthranukul et al. "Modulation of Intestinal Serotonin Production and Serotonin Transporter by Lactobacillus reuteri and Bifidobacterium dentium" Journal of Pediatric Gastroenterology and Nutrition, (2018), 66(2):102.
Wang et al. "Lactobacillus rhamnosus GG supernatant upregulates serotonin transporter expression in intestinal epithelial cells and mice intestinal tissues" Neurogastroenterology and Motility, GB, (2015) 27(9):1239-1248.
Chabbi-Achengli, Yasmine, et al. "Decreased osteoclastogenesis in serotonindeficient mice", PNAS, vol. 109, No. 7, pp. 2567-2572 (2012).
Cote, Francine, et al. "Recent advances in understanding serotonin regulation of cardiovascular function", Trends in Molecular Medicine, vol. 10, No. 5, 232-238 (2004).
Israelyan, Narek, et al. "Effects of Serotonin and Slow-release 5-HTP on Gastrointestinal Motility in a Mouse Model of Depression", Gastroenterology, 157(2): 507-521 (2019).
Lyte, Mark, "Probiotics function mechanistically as delivery vehicles for neuroactive compounds: Microbial endocrinology in the design and use of probiotics", Bioessays 33: pp. 574-581 (2011).
Naskali, Emmi, et al. "Serotonin and tryptophan metabolites, autoantibodies and gut microbiome in APECED", Endocrine Connections, vol. 8, pp. 69-77 (2019).
Oleskin, Alexander V., et al. "Lactic-Acid Bacteria Supplement Fermented Dairy Products with Human Behavior-Modifying Neuroactive Compounds", Journal of Pharmacy and Nutrition Sciences, vol. 4, No. 3, pp. 199-206 (2014).
Oleskin, A. V., et al. "Role of Neuromediators in the Functioning of the Human Microbiota: "Business Talks" among Microorganisms and the Microbiota-Host Dialogue", Microbiology, vol. 85, No. 1, pp. 1-22 (2016).
Özoğul, Fatih, et al. "The Function of Lactic Acid Bacteria on Biogenic Amines Production by Food-Borne Pathogens in Arginine Decarboxylase Broth", Food Sci. Technol. Res., vol. 18 (6), pp. 795-804 (2012).

(Continued)

Primary Examiner — Suzanne M Noakes
Assistant Examiner — Jae W Lee
(74) Attorney, Agent, or Firm — Myers Bigel, P.A.

(57) ABSTRACT

The invention relates to selection of bacterial strain for use in treating serotonin deficiency and/or a disease related to serotonin deficiency by culturing bacteria of a lactic acid producing bacterial strain, under aerobic conditions, in a culture medium comprising tryptophan. Any serotonin produced by the bacteria of the lactic acid producing bacterial strain in the culture medium is detected and the lactic acid producing bacterial strain is selected as effective in treating serotonin deficiency and/or a disease related to serotonin deficiency in a subject if serotonin is detected in the culture medium.

18 Claims, 11 Drawing Sheets

(56) References Cited

OTHER PUBLICATIONS

Pallin, Anton, "Improving the functional properties of Lactobacillus reuteri", Doctoral thesis, Swedish University of Agricultural Sciences, Uppsala 2018 (91 pages).

Paul-Savoie, Emilie, et al. "A Deficit in Peripheral Serotonin Levels in Major Depressive Disorder but Not in Chronic Widespread Pain", The Clinical Journal of Pain, vol. 27, No. 6, pp. 529-534 (2011).

Yekehtaz, Habibeh, et al. "Cardiovascular Considerations in Antidepressant Therapy: An Evidence-Based Review", The Journal of Tehran University Heart Center, vol. 8, No. 4, pp. 169-176 (2013).

Opposition filed in corresponding European Application No. 20807535.8 dated May 22, 2024.

Beck, Bo Ram, et al., "Multidisciplinary and Comparative Investigations of Potential Psychobiotic Effects of Lactobacillus Strains Isolated From Newborns and Their Impact on Gut Microbiota and Ileal Transcriptome in a Healthy Murine Model", Front. Cell. Infect. Microbiol. 9:Article 269 (Jul. 25, 2019) 12 pages.

Riezzo, G., et al., "Effects of long-term administration of Lactobacillus reuteri DSM-17938 on circulating levels of 5-HT and BDNF in adults with functional constipation", Beneficial Microbes 10(2):137-147 (Mar. 13, 2019).

Van Tassell, Maxwell L, et al., "Lactobacillus Adhesion to Mucus", Nutrients 3:613-636 (May 20, 2011).

* cited by examiner

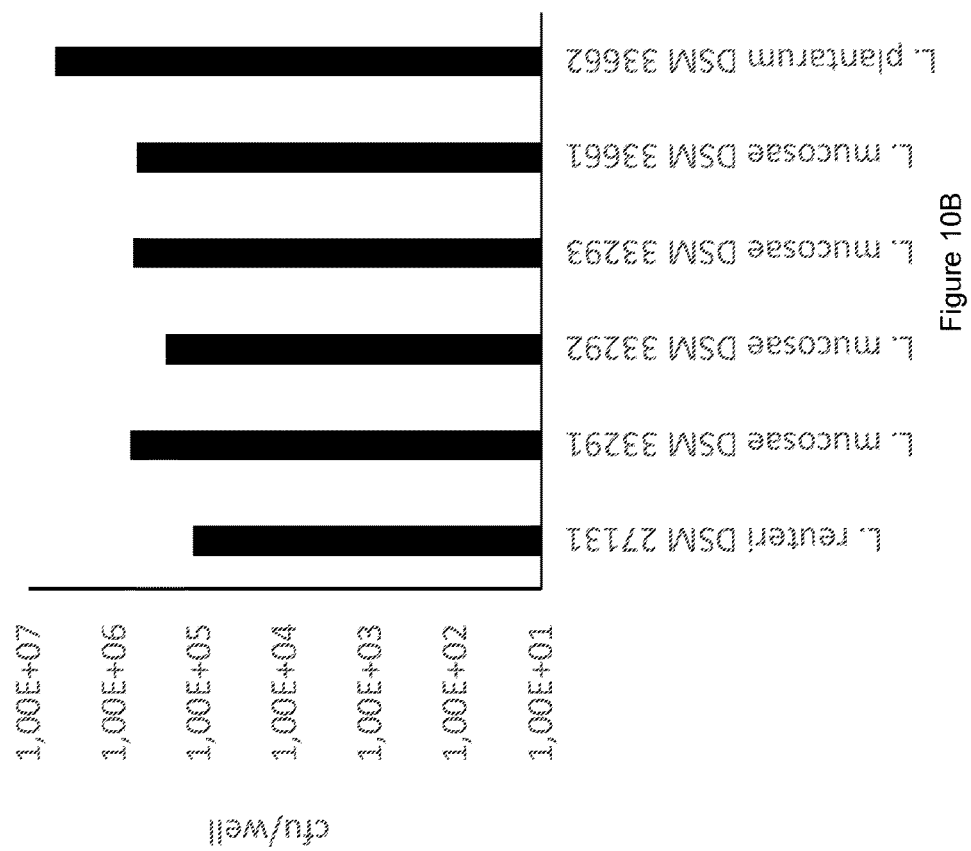
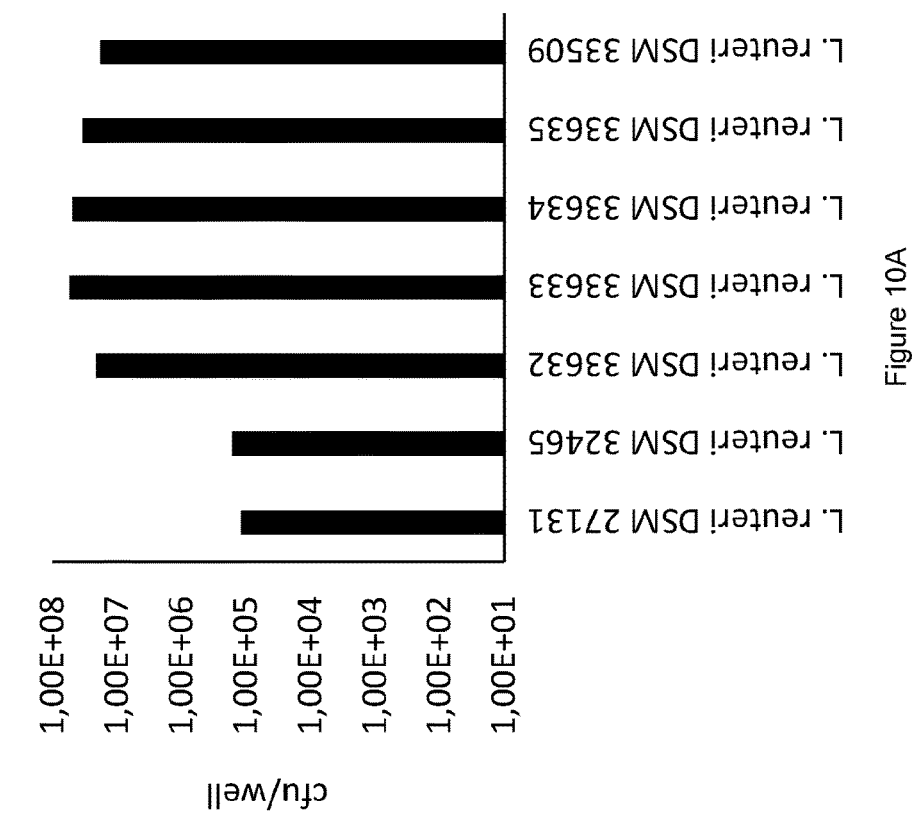
Figure 10A
Figure 10B

SEROTONIN PRODUCING BACTERIA

TECHNICAL FIELD

The present invention generally relates to lactic acid producing bacteria, and in particular to screening such lactic acid producing bacteria for production of serotonin and the use of such lactic acid producing bacteria in the treatment of serotonin deficiency and in the treatment of disorders and diseases related to serotonin deficiency.

STATEMENT OF PRIORITY

This application is a 35 U.S.C. § 371 national phase application of International Application Serial No. PCT/US2020/051075, filed on Nov. 6, 2020, which claims the benefit, under 35 U.S.C. § 119 (b), of Swedish Application No. 1951292-0, filed on Nov. 8, 2019, the entire contents of each of which is incorporated by reference herein.

BACKGROUND

It is well established that interactions between host and gut microbes are fundamental to health and well-being of the host. Intestinal microbiota generates metabolites that provide the host with nutrients but may also be involved in the immune response and in regulation and development of the host's immune system.

Lactobacilli and other lactic acid producing bacteria, such as bifidobacteria, are commonly used as probiotics in various types of foods, for example yoghurt. Growth and colonization of harmful microorganisms can be prevented by such lactic acid producing bacteria through their own colonization inside the intestinal ecosystem, such as through formations of biofilms, through competition of available nutrients and/or through production of specific substances, such as hydrogen peroxide, bacteriocins and/or organic acids, including lactic and acetic acid, that lowers the intestinal pH.

Serotonin, or 5-hydroxytryptamine (5-HT), is a bioamine synthetized from the aromatic amino acid tryptophan, which has several physiological functions including in behavior, platelet activation and coagulation, gut transit, enteric nervous system (ENS) maturity, development, homeostasis and activity, intestinal immune system activity, energetic metabolism (fasting adaptation, browning and lipolysis of adipose tissue, hepatic glucose production, insulin secretion), gut-brain axis activity and bone metabolism and homeostasis. In humans, serotonin is primarily found in the gastrointestinal (GI) tract, in blood platelets, and in the central nervous system (CNS). In mammalian cells, serotonin production is enabled by the rate limiting enzyme tryptophan hydroxylase (TPH), which produces 5-hydroxytryptophan (5-HTP). 5-HTP is the immediate precursor of serotonin and is converted into serotonin by the aromatic L-amino-acid decarboxylase (MDC). There are two isoforms of TPH; TPH1 is primarily expressed in peripheral tissues, whereas TPH2 is primarily expressed in the brain (CNS) and in ENS neurons. TPH1 is the enzyme responsible for most of the endogenous serotonin production, and this enzyme is expressed by highly specialized endocrine cells within the GI tract, called enterochromaffin (EC) cells. It has been clearly demonstrated that the gut microbiota is involved in regulating the endogenous host serotonin production by metabolic signaling to the EC cells. Metabolites, such as short-chain fatty acids and secondary bile acids, from gut microbiota have been shown to induce the expression of TPH1 in mouse EC cells, and correspondingly, the levels of endogenously produced serotonin are directly regulated by these bacteria. Consequently, serum serotonin levels are substantially reduced in mice reared in the absence of microbial colonization, such as in germ-free (GF) mice as compared to in conventionally colonized control animals with a regular microbiota.

Serotonin deficiency occurs when the body does not have sufficient serotonin, which can happen for several reasons. Serotonin deficiency locally in the gut or in the remaining body can cause pathological conditions including depression, anxiety, obsessive-compulsive disorder, irritable bowel syndrome, cardiovascular disease, osteoporosis, abnormal gastrointestinal motility, abnormal platelet aggregation, abnormal platelet activation, and abnormal immune response. Serotonin deficiency, thus, presents a health risk. Various drugs have been developed to treat serotonin deficiency, such as selective serotonin reuptake inhibitors (SSRIs) and monoamine oxidase (MAO) inhibitors. However, these drugs are often associated with more or less severe side effects, such as diarrhea, constipation, insomnia, dizziness, and a dry mouth. In addition, these drugs are not suitable for everyone and SSRIs, for instance, should not be taken by pregnant women, when breastfeeding, when a person is under 18 years of age, when a person has diabetes, epilepsy, or kidney disease. In addition, both SSRIs and MAO inhibitors may interact with other medicines, such as painkillers, other antidepressants, as well as with cold and allergy medications, and can therefore cause serious detrimental reactions. MAO inhibitors can also interact with a number of foods and beverages causing dangerously high blood pressures. These characteristics make the known serotonin deficiency drugs unsuitable for a large group of patients and there is therefore a great need to provide alternative effective treatments for serotonin deficiency, or serotonin deficiency-associated disorders with no or little side effects.

Taken together, there is a need for safe methods that can increase serotonin levels in patients with serotonin deficiency and that can be used in treatment of a serotonin deficiency and diseases or disorders related to serotonin deficiency.

SUMMARY

It is a general objective to screen for lactic acid producing bacterial strains for use in treating serotonin deficiency and/or a disease related to serotonin deficiency.

It is a particular objective to screen for lactic acid producing bacterial strains that are capable of producing serotonin locally within the gastrointestinal tract in more oxygenated niches of the intestine, such as close to the mucosa.

These and other objectives are met by the embodiments as disclosed herein.

The present invention is defined in the independent claims. Further embodiments of the invention are defined in the dependent claims.

An aspect of the embodiments relates to a method for selecting a bacterial strain for use in treating serotonin deficiency and/or a disease related to serotonin deficiency. The method comprises culturing, under aerobic conditions, bacteria of a lactic acid producing bacterial strain in a culture medium comprising tryptophan. The method also comprises detecting any serotonin produced by the bacteria of the lactic acid producing bacterial strain in the culture medium or a sample thereof. The method further comprises selecting the lactic acid producing bacterial strain as effective in treating serotonin deficiency and/or a disease related to serotonin deficiency in a subject if serotonin is detected in the culture medium or the sample thereof.

Another aspect of the embodiments relates to a method for selecting a bacterial strain for use in treating serotonin deficiency and/or a disease related to serotonin deficiency. The method comprises feeding a germ free Tph1−/− subject with bacteria of a lactic acid producing bacterial strain. The method also comprises detecting any serotonin produced by the bacteria of the lactic acid producing bacterial strain in a body sample taken from the germ free Tph1−/− subject. The method further comprises selecting the lactic acid producing bacterial strain as effective in treating serotonin deficiency and/or a disease related to serotonin deficiency in a subject if serotonin is detected in the body sample. Another aspect of the embodiments relates to a lactic acid producing bacterial strain capable of producing and extracellularly releasing serotonin under aerobic conditions for use in treatment of serotonin deficiency and/or a disease related to serotonin deficiency in a subject.

Further aspects of the embodiments relate to *Lactobacillus mucosae* DSM 33291, *Lactobacillus mucosae* DSM 33292, *Lactobacillus mucosae* DSM 33293, *Lactobacillus mucosae* DSM 33661, *Lactobacillus reuteri* DSM 33509, *Lactobacillus reuteri* DSM 33632, *Lactobacillus reuteri* DSM 33633, *Lactobacillus reuteri* DSM 33634, *Lactobacillus reuteri* DSM 33635, *Lactobacillus plantarum* DSM 33295, and *Lactobacillus plantarum* DSM 33662 and use thereof as a medicament and for use in treatment of serotonin deficiency and/or a disease related to serotonin deficiency.

Lactic acid producing bacterial strains selected according to the embodiments can produce serotonin in the gastrointestinal system of mammals. In particular, the lactic acid producing bacterial strains selected according to the invention are capable of producing serotonin in conditions of more oxygenated niches of the intestine, for example close to the epithelial lining of the intestine where the serotonin receptors and/or the serotonin transporters (SERT) are expressed and also where enteroendocrine cells, such as enterochromaffin cells, are located. This microbially produced serotonin is bioactive and has an effect locally within the gastrointestinal tract but may also have effects peripherally with regards to the gastrointestinal system. Accordingly, serotonin produced by gut bacterial strains can be used in the treatment of serotonin deficiency and/or a disease related to serotonin deficiency in a subject.

BRIEF DESCRIPTION OF THE DRAWINGS

The embodiments, together with further objects and advantages thereof, may best be understood by making reference to the following description taken together with the accompanying drawings, in which:

FIG. 10 illustrates the mucus adhesion ability of serotonin producing lactic acid bacterial strains *L. reuteri* DSM 27131, DSM 32465, DSM 33632, DSM 33633, DSM 33634, DSM 33635, and DSM 33509, *L. mucosae* DSM 33291, DSM 33292, DSM 33293, and DSM 33661, and *L. plantarum* DSM 33662. *L. reuteri* DSM 27131, which is capable of producing serotonin under aerobic conditions in vitro and which is able to contribute to the systemic pool of serotonin in vivo, is also capable of attaching to mucus (A, B). Mucus adhesion was also observed for all other tested *L. reuteri*, *L. mucosae* and *L. plantarum* strains (A, B). The results indicate that these serotonin-producing bacterial strains are also able to attach to the intestinal mucosa.

DETAILED DESCRIPTION

Figure 1A:
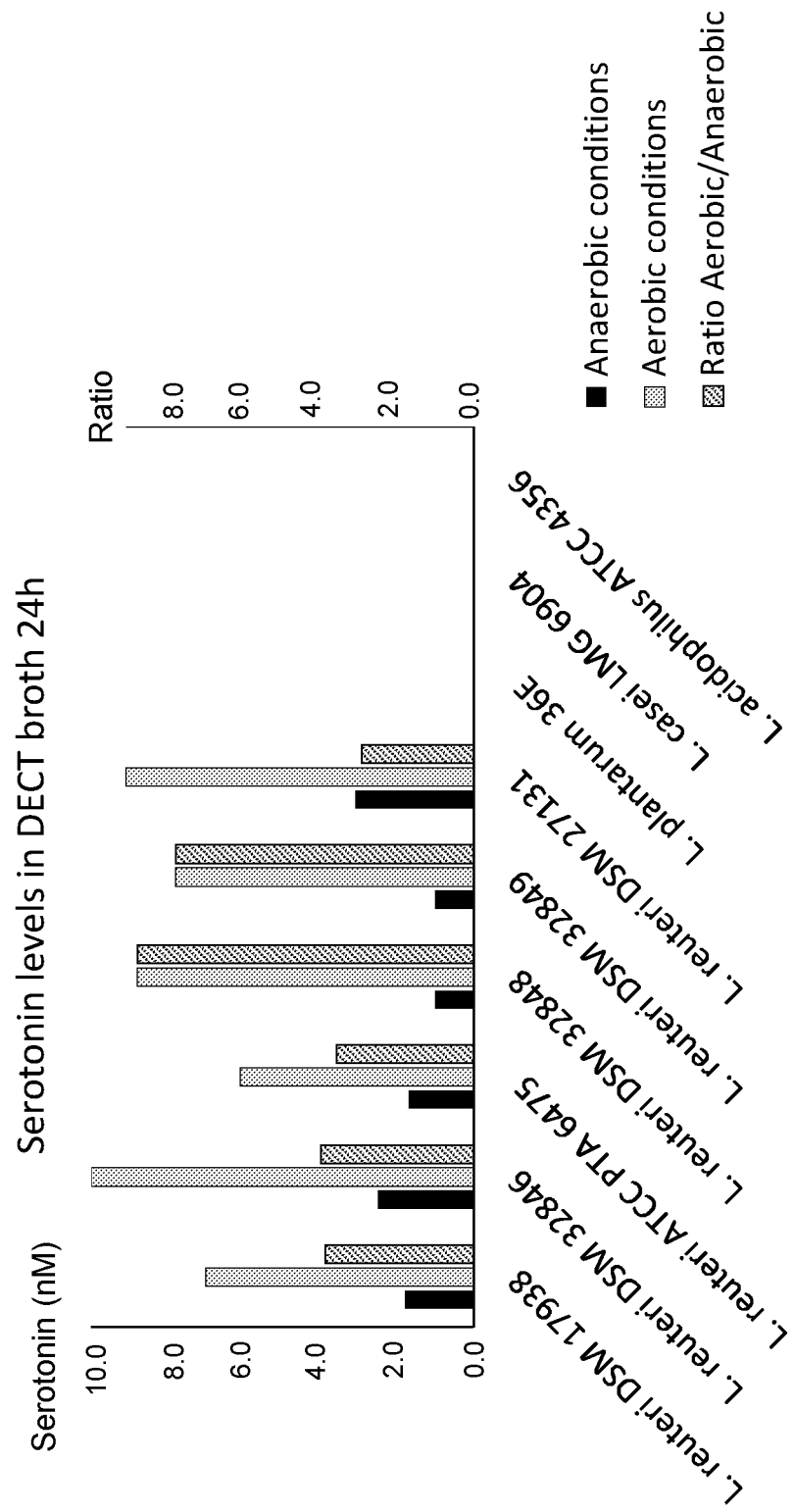
FIG. 1. Assessment of serotonin production by lactic acid producing bacterial strains. (A) The levels of serotonin were measured in the culture medium (broth) of *Lactobacillus reuteri*, *Lactobacillus plantarum*, *Lactobacillus casei*, and *Lactobacillus acidophilus* bacterial strains after culturing them under anaerobic and aerobic conditions in tryptophan modified decarboxylase (DECT) broth. All tested *L. reuteri* bacterial strains were found to produce serotonin under anaerobic conditions, and they were found to produce even more serotonin under aerobic conditions, whereas no serotonin production was observed by the bacterial strains *L. plantarum* 36E, *L. casei* LMG 6904, and *L. acidophilus* ATCC 4365 under any of the corresponding conditions in vitro. The ratio between aerobic and anaerobic serotonin production was calculated for each bacterial strain. All investigated *L. reuteri* bacterial strains were better serotonin producers under aerobic conditions in vitro compared to under anaerobic conditions. (B) The serum serotonin concentration was measured in blood samples obtained from the vena cava of germ-free (GF) Tph1−/− mice, and from GF Tph1−/− mice that had been fed (inoculated) with either *L. reuteri* DSM 17938, *L. reuteri* DSM 27131 or *L. casei* LMG 6904 (n=3-6/group). Data in the graph is presented as box plots, and each dot represents one mouse, showing maximum, minimum, median, and interquartile range. The graph shows that serotonin levels, which are very low in GF Tph1−/− mice, are restored in these mice after inoculation with *L. reuteri* bacterial strains. No increase in serotonin levels was, however, observed in the serum samples obtained from mice inoculated with *L. casei* LMG 6904, indicating that this bacterial strain does not produce serotonin in vivo. The normality of each group was analyzed before the statistical significance was evaluated by Student's t test (if data was normally distributed) or Mann-Whitney test. When more than two groups were compared, data was analyzed using one-way Anova followed by post hoc Tukey's multiple comparisons tests if data was normally distributed, otherwise Kruskal-Wallis test followed by post hoc Dunn's multiple comparisons were performed. The level of significance was set at *p<0.05.

TPH1 is the enzyme responsible for endogenous serotonin production in the gastrointestinal tract. In spite of this, some serotonin remains when the Tph1 gene is deleted in a mouse model (i.e., resulting in Tph1–/– animals), indicating that a portion of the serotonin is not produced by endogenous TPH1-mediated mechanisms. The inventors of the invention herein surprisingly found that when re-deriving Tph1–/– mice as germ free (i.e., animals deficient of a gastrointestinal microbiota), they were almost completely depleted of serotonin. The next surprising discovery was that inoculation of germ free Tph1–/– mice with wildtype mouse caecal microbiota or with a serotonin-producing *Lactobacillus* bacterial strain was sufficient to restore serotonin levels in the gut. These novel discoveries suggested that bacteria within the normal gastrointestinal tract are not only capable of affecting the endogenous (host) serotonin production, as was previously known, but surprisingly also that they are capable of their own production of serotonin locally within the gastrointestinal tract. The inventors then found that certain strains of lactic acid bacteria are capable of producing serotonin under both anaerobic and aerobic conditions in vitro. In addition, for certain strains, the serotonin production was greatly improved under aerobic conditions compared to the production of serotonin under anaerobic conditions. The present invention is, thus, based on the finding that certain bacterial strains, in particular certain strains of lactic acid producing bacteria, which are normally anaerobic, can produce serotonin under aerobic conditions. An objective is therefore to screen for and select such bacteria that are capable of producing and extracellularly releasing serotonin under aerobic conditions. These bacteria capable of producing and extracellularly releasing serotonin under aerobic condition are in particular adapted to locally produce and release serotonin within the gastrointestinal tract of a subject, such as in the more oxygenated niches of the intestine close to the mucosa/epithelial lining of the intestine. At these more oxygenated niches of the intestine, enteroendocrine cells, such as enterochromaffin cells, are located and serotonin receptors and/or the serotonin transporters (SERT) are expressed. Any selected bacterial strain is preferably capable of adhering to mucus, or at least be present at, or close to, the mucosa where they are exposed to a comparatively high oxygen partial pressure, which is a characteristic to the oxygenated niches of the gastrointestinal tract.

Screening of such bacteria may be done in vitro by culturing lactic acid producing bacterial strains under aerobic conditions or under anaerobic and aerobic conditions and selecting bacteria, which are identified as being capable of producing serotonin under aerobic conditions only, or under both anaerobic and aerobic conditions. Selected bacteria can then, when administered to a subject, be used to produce serotonin locally within the gastrointestinal tract of that subject to increase levels of serotonin in subjects with serotonin deficiency or suffering from a disease or disorder related to serotonin deficiency.

Screening of such bacteria may also be done in vivo using a germ free (GF) Tph1-/- mammal subject that is fed the lactic acid producing bacterial strains. Serotonin production by the lactic acid bacterial strain in the gastrointestinal tract of the GF Tph1-/- subject can then be assessed or analyzed in a body sample taken from the GF Tph1-/- subject to determine whether the lactic acid bacterial strain is effective in treating serotonin deficiency or a disease or disorder related to serotonin deficiency.

Furthermore, microbially produced serotonin is bioactive and has effects not only locally within the gastrointestinal tract but can also be transported across the epithelial lining of the gastrointestinal tract into the systemic circulation where it is capable of acting peripherally with regard to the gastrointestinal system, i.e., having systemic effects. For bacterially produced serotonin to reach the systemic circulation it is preferred that the production of serotonin takes place close to the intestinal mucosa and the intestinal epithelium, where oxygen levels are normally higher compared to in the gut lumen. Therefore in a particular embodiment, serotonin producing bacteria selected according to the embodiments are preferably also capable of adhering to mucus in the more oxygenated niches of the gastrointestinal tract, or at least to be present at or close to the mucosa, and/or possibly also colonizing the mucosa of the gastrointestinal tract, securing the close proximity between bacteria and the epithelial cells of the gastrointestinal tract.

In addition, if produced close to the epithelial cells of the gastrointestinal tract, serotonin produced by lactic acid producing bacterial strains is capable of local actions on the gastrointestinal tract itself, such as affecting maturity of, and communication within, the enteric nervous system (ENS). The ENS consists of glial and nervous cells embedded in the lining of the gastrointestinal tract, and this nervous system is responsible, for instance, for the motor control of the gastrointestinal system and for secretion of gastrointestinal enzymes. In addition, this nervous system communicates through many neurotransmitters, which are similar to communication in the central nervous system, including via acetylcholine, dopamine, and serotonin.

Lactic acid producing bacterial strains that produce serotonin in the gastrointestinal tract can, thus, be used to treat serotonin deficiency and/or disorders and diseases related to serotonin deficiency locally within the gastrointestinal tract, but also in other parts of the body when serotonin is transported over the gastrointestinal lining into the systemic circulation and further into peripheral tissues.

Lactic acid producing bacterial strains, also referred to as lactic acid bacterial strains, are gram-positive, low-GC, acid-tolerant, generally non-sporulating, non-respiring and either rod-shaped or spherical bacteria that are capable of producing lactic acid as the major metabolic end product of carbohydrate fermentation. Lactic acid producing bacteria grow anaerobically, but unlike most anaerobes, they are capable of growing also in the presence of oxygen as aerotolerant, or relative oxygen-tolerant anaerobes. Lactic acid producing bacteria are generally recognized as safe (GRAS) and include genera in the order Lactobacillales, which includes *Lactobacillus, Leuconostoc, Pediococcus, Lactococcus* and *Streptococcus*, in addition to *Aerococcus, Carnobacterium, Enterococcus, Oenococcus, Tetragenococcus, Vagococcus*, and *Weissella*, and also the genera *Bifidobacterium* in the order of Bifidobacteriales.

In the last decades new analytical tools have enabled scientists to discover many new bacterial species as well as realizing that the species historically grouped under *Lactobacillus* were too different from each other. To keep the probiotic groups accurate and organized, the genus *Lactobacillus* was therefore split into 25 different genera. As a result, many probiotics have recently been given new genus names. Therefore, an alternative genus name for *Lactobacillus reuteri* is *Limosilactobacillus reuteri*, an alternative genus name for *Lactobacillus mucosae* is *Limosilactobacillus mucosae*, an alternative genus name for *Lactobacillus plantarum* is *Lactiplantibacillus plantarum*, and alternative genus name for *Lactobacillus casei* is *Lacticaseibacillus casei*.

Figure 5:
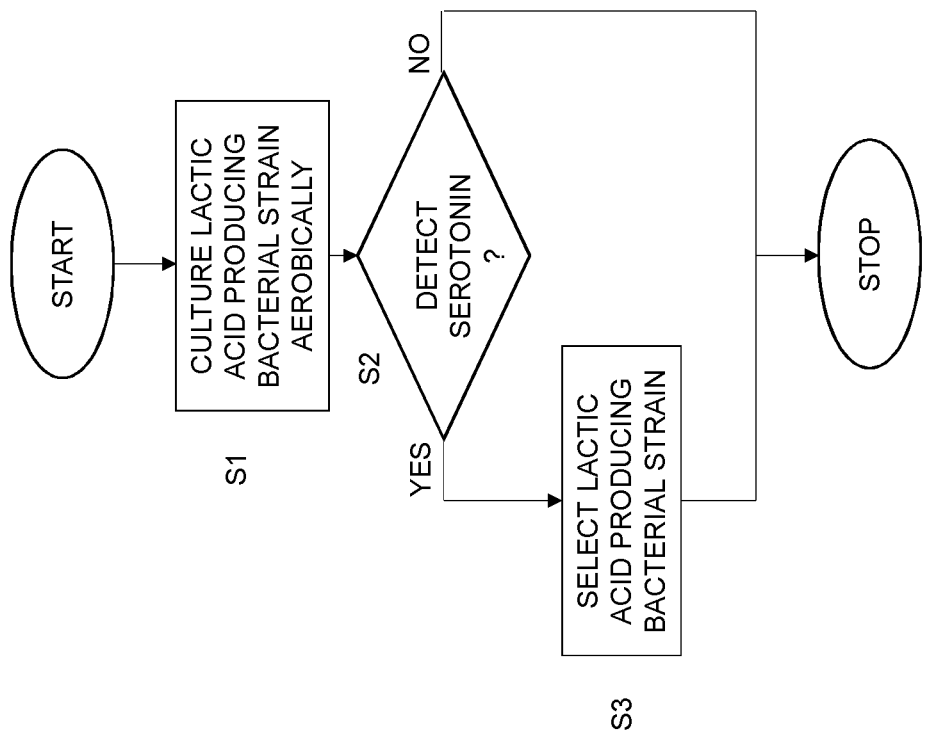
FIG. 5 is a flow chart illustrating a method for selecting a bacterial strain according to an embodiment.

FIG. 5 is a flow chart illustrating a method for selecting a bacterial strain for use in treating serotonin deficiency and/or a disease related to serotonin deficiency. The method starts in step S1, which comprises culturing bacteria of a lactic acid producing bacterial strain, under aerobic conditions, in a culture medium comprising tryptophan. A next step S2 comprises detecting any serotonin produced by the bacteria of the lactic acid producing bacterial strain in the culture medium or a sample thereof. The method also comprises selecting, in step S3, the lactic acid producing bacterial strain as effective in treating serotonin deficiency and/or a disease related to serotonin deficiency in a subject if serotonin is detected in the culture medium or the sample thereof.

Such bacteria are, thus, selected for their capability of producing serotonin in conditions of more oxygenated niches of the intestine, for example, close to the gastrointestinal mucosa and the epithelial lining of the intestine where the serotonin receptors and/or the serotonin transporters (SERT) are expressed and also where specific enteroendocrine cells, such as enterochromaffin cells, are located.

The selection method as shown in FIG. 5 comprises cultivation and testing of lactic acid producing bacterial strains in a culture medium comprising tryptophan. Tryptophan is the starting material in the production of serotonin. In more detail, tryptophan hydroxylase (TPH) (EC 1.14.16.4), of which there are two isoforms TPH1 and TPH2, synthesizes 5-hydroxytryptophan (5-HTP) from tryptophan. 5-HTP is in turn converted into serotonin (5-HT) by aromatic L-amino acid decarboxylase (AADC) (EC 4.1.1.28). Accordingly, the culture medium, in which bacteria of the lactic acid producing bacterial strain(s) to be tested are cultured, comprises tryptophan as starting material for any production of serotonin by the lactic acid producing bacterial strain(s).

According to the invention, bacteria of the lactic acid producing bacterial strain is inoculated in the tryptophan-comprising culture medium under aerobic conditions. Hence, the selected lactic acid producing bacterial strain should be capable of producing serotonin at least under aerobic conditions. Differences in oxygen partial pressure can have a significant effect on bacterial metabolism in terms of shifting the bacterial metabolism of aromatic L-amino acids, such as tryptophan, into different metabolites. This means that a given lactic acid producing bacterial strain produces different metabolites from tryptophan when cultured at different oxygen partial pressures, i.e., aerobic conditions vs. anaerobic conditions. In other words, lactic acid producing bacteria that are capable of producing serotonin under aerobic conditions do not necessarily produce serotonin under anaerobic conditions and conversely, lactic acid producing bacteria that are capable of producing serotonin under anaerobic conditions do not necessarily produce serotonin under aerobic conditions.

The oxygen partial pressure in the intestines and in the stomach is generally higher close to the intestinal mucosa as compared to internal parts of the small intestine (consisting of duodenum, jejunum and ileum) and the large intestine (colon consisting of caecum, rectum and anal canal). This means that the oxygen present at the intestinal epithelium corresponds to a gradient, with higher concentrations of oxygen close to the mucosa and lower concentrations of oxygen towards the luminal side. Step S1 in FIG. 5 is, thus, performed under aerobic conditions, i.e., in the presence of oxygen, in order to mimic the aerobic conditions, or oxygenated niches, close to the intestinal mucosa. The lactic acid producing bacterial strains selected according to the method shown in FIG. 5 are, preferably also, capable of adhering to and/or colonizing the intestinal mucosa or epithelial lining of the gastrointestinal tract or at least be present at or close to the intestinal mucosa where they are exposed to a comparatively high oxygen partial pressure as is discussed further in connection with FIG. 7. This means that in order to produce serotonin in vivo in the gastrointestinal system of a subject and for the microbially produced serotonin to be efficiently taken up from the gastrointestinal tract to the systemic circulation by the subject, the lactic acid producing bacterial strain selected in the method as shown in FIG. 5 should be capable of producing serotonin in aerobic conditions mimicking the conditions at or close to the intestinal mucosa.

The terms "anaerobe" and "anaerobic" as used herein in connection with anaerobic culturing conditions encompass such culturing conditions that are characterized by oxygen ($O_2$) free conditions i.e., the dissolved oxygen and head space of culture tubes has 0% or 0 ppm $O_2$, at least close to 0% or 0 ppm $O_2$. As an illustrative example, anaerobic culturing could involve culturing lactic acid producing bacteria in a culture medium in a closed culture container such as gas tight serum vials or hungate tubes. The culture medium may optionally be degassed prior to adding the lactic acid producing bacteria. In addition, or alternatively, the culture container may be purged, for instance with $N_2$, prior to or following closure of the container or alternatively boiled for 15-20 minutes and cooled down under nitrogen flow to remove any dissolved oxygen present in the media or any enclosed gas volume in the closed culture container.

Correspondingly, the terms "aerobe" and "aerobic" as used herein in connection with aerobic culturing conditions encompass such culturing conditions that are characterized by the presence of free oxygen ($O_2$) in the head space of culture tubes corresponding to 100% saturation or 8.87 ppm of dissolved oxygen. The initial amount of dissolved oxygen in the growth medium could range from any detectable level, such as from 2.41 ppm corresponding to 29.3% saturation, preferably from 4.8 ppm corresponding to 64% saturation, and preferably up to 9 ppm corresponding to ~103% saturation of dissolved oxygen. Levels of oxygen in the atmosphere is around 21%. As an illustrative example, aerobic culturing could involve culturing lactic acid producing bacteria in a culture medium in an open culture container. Alternatively, the lactic acid producing bacteria could be cultured in a closed culture container if oxygen is added to the closed culture container.

Step S1 in FIG. 5 could be performed during a predetermined period of time. For instance, bacteria of the lactic acid producing bacterial strain could be incubated and cultured aerobically in the culture medium for at least 1 hour, for at least multiple, i.e., at least two, hours, such as 2, 3, 4, 5, 6, 7, 8, 9, 10, 11 or 12 hours. The bacteria of the lactic acid producing bacterial strain could also be cultured for longer periods of time, such as 24 hours, 36 hours, 48 hours or 60 hours as illustrative, but non-limiting, examples.

In an embodiment, step S2 in FIG. 5 comprises taking a sample from the culture medium and detecting any serotonin produced by the bacteria of the lactic acid producing bacterial strain in the sample. In an embodiment, the sample of the culture medium is a cell-free sample. In such an embodiment, any cells, in particular bacterial cells, present in the sample are first removed, such as by subjecting the sample to one or more centrifugations, such as 10,000×g for 1-4 minutes, such as 2 minutes, in order to separate the sample into a cell-containing pellet and a supernatant that may comprise serotonin. Step S2 in FIG. 5 then also comprises detecting any serotonin produced by the lactic acid producing bacterial strain in the supernatant. In addition, or alternatively, the culture medium sample may be filtrated through one or more filters that are configured to capture the bacteria but at the same time allow serotonin in the culture medium sample to pass through the filter(s). In such an embodiment, the detection of serotonin could be done in the filtrate.

Serotonin can be measured in the culture medium, the sample or the supernatant using any known serotonin-measuring assay or technique. For instance, serotonin can be measured using an Enzyme-Linked Immunosorbent Assay (ELISA) or a mass spectrometry (MS) assay.

If the measurement of serotonin results in identification of serotonin in the culture medium, in the sample or in the supernatant from a specific lactic acid producing bacterial strain, this confirms that the lactic acid producing bacterial strain is capable of producing and extracellularly releasing serotonin and the tested lactic acid producing bacterial strain will be selected in step S3 of FIG. 5 as being effective in producing serotonin and thereby also effective in treating a disease related to serotonin deficiency in a subject.

Thus, by detecting presence of serotonin in the culture medium, which also encompasses detecting presence of serotonin in a sample of the culture medium or a processed sample of the culture medium, such as the supernatant following centrifugation of a culture medium sample or a filtrate following filtration of the culture medium sample, in step S2, the bacteria of the lactic acid producing bacterial strain is not only capable of producing serotonin but also capable of extracellularly releasing serotonin into the culture medium. Such an extracellular release of serotonin is important for use of the lactic acid producing bacterial strain for treatment of serotonin deficiency and/or a disease related to serotonin deficiency in a subject, since the bacterially produced serotonin needs to reach the subject either locally in the gastrointestinal tract and/or being absorbed by the epithelium to reach the systemic circulation.

In an embodiment, the culture medium comprises a carbon source in addition to tryptophan. Any carbon source that can be used by the lactic acid producing bacterial strain(s) to be tested could be included in the culture medium, including, but not limited to, glucose. The culture medium preferably also comprises a source of nitrogenous compounds, such as amino acids; manganese; sulfate; vitamins and growth factors, such as in the form of a yeast extract and/or a beef extract. An example of a culture medium that could be used in the method of FIG. 5 is a novel tryptophan modified decarboxylase (DECT) broth designed to promote tryptophan decarboxylation and microbial production of serotonin. Such a DECT broth or culture medium comprises tryptophan, glucose, beef extract and yeast extract.

In an embodiment, the culture medium comprises at least 0.4 g/100 mL tryptophan, preferably at least 0.5 g/100 mL, such as at least 0.6 g/100 mL, at least 0.7 g/100 mL, and more preferably at least 0.8 g/100 mL, such as at least 0.9 g/100 mL or about 1 g tryptophan per 100 mL culture medium.

A currently preferred culture medium, the DECT broth, mentioned above preferably comprises tryptophan 1 g/100 mL, glucose 0.05 g/100 mL, beef extract 0.5 g/100 mL and yeast extract 0.1 g/100 mL.

Figure 6:
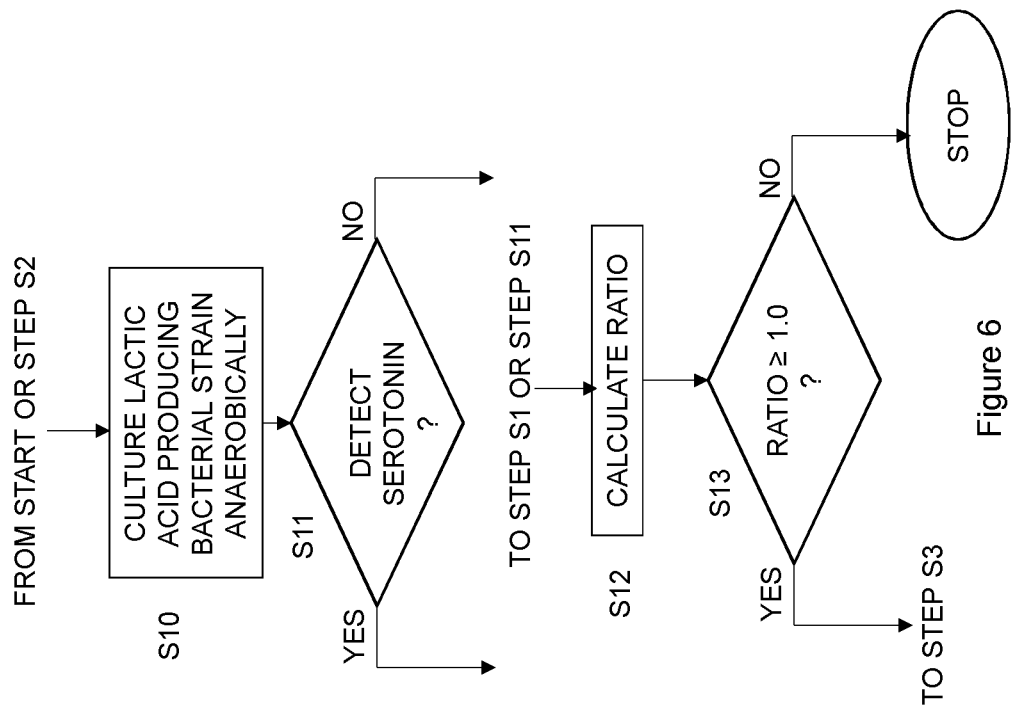
FIG. 6 is a flow chart illustrating additional, optional steps to the method shown in FIG. 5 according to an embodiment.

In an embodiment, the method comprises additional steps as shown in FIG. 6. In such an embodiment, the method starts in step S10 or continues from step S2 in FIG. 5. Step S10 comprises culturing, under anaerobic conditions, bacteria of the lactic acid producing bacterial strain in a culture medium comprising tryptophan. The method then continues to step S11, which comprises detecting any serotonin produced by the bacteria of the lactic acid producing bacterial strain in the culture medium or a sample thereof when cultured under anaerobic conditions. Step S10 is preferably conducted in a similar way to what has been described in the foregoing in connection with step S1 in FIG. 5, including culturing time, culture medium, etc., but with the difference that in step S1 in FIG. 5, bacteria of the lactic acid producing strain are cultured under aerobic conditions, whereas in step S10 in FIG. 6, bacteria of the lactic acid producing strain are cultured under anaerobic conditions. Correspondingly, the detection of serotonin in step S11 in FIG. 6 could be performed in the same way as discussed in connection with step S2 in FIG. 5.

This embodiment preferably also comprises a step S12 as shown in FIG. 6. This step S12 comprises calculating a ratio or quotient between a concentration of serotonin detected in the culture medium or the sample thereof when cultured under aerobic conditions (see step S2 in FIG. 5) and a concentration of serotonin detected in the culture medium or the sample thereof when cultured under anaerobic conditions (see step S11 in FIG. 6). The method then continues to optional step S13, which compares the calculated ratio or quotient with a threshold value, such as 1.0. If the ratio or quotient is equal to or larger, preferably larger, than the threshold value, such as equal to or larger than 1.0, preferably larger than 1.0, the method continues to step S3 in FIG. 5. Hence, in this embodiment, step S3 comprises selecting the lactic acid producing bacterial strain as effective in treating serotonin deficiency and/or the disease related to serotonin deficiency in a subject if the ratio is equal to or larger than 1.0, preferably larger than 1.0.

In a particular embodiment, the threshold value to which the ratio or quotient is compared in the optional step S13 is 1.5, preferably 2.0, such as 2.5, and more preferably 3.0, such as 3.5, or even higher, such as 4.0, 4.5, 5.0, 5.5, 6.0, 6.5, 7.0, 7.5, 8.0, 8.5, 9.0, 9.5 or even 10.0. The threshold may, in some embodiments be even higher such as 15, 20, 25, 30, 40 or 50 or even higher.

Bacteria of certain lactic acid producing bacterial strains are significantly more efficient producers of serotonin when cultured in aerobic conditions as compared to when cultured in anaerobic conditions. In some lactic acid producing bacterial strains the amount of serotonin detected in the culture medium of the sample thereof is very low and may even be below the detection limit of the assay used to detect serotonin, i.e., what is possible to accurately detect using the particular assay. Such lactic acid producing bacterial strains will, hence, have very high ratios or quotients. In an optional embodiment, the method as shown in FIG. 6 therefore comprises an additional, optional step (not shown in FIG. 6) of determining whether the concentration of serotonin detected in step S11 in the culture medium or the sample thereof when cultured under anaerobic conditions is below a threshold value, such as the detection limit of the assay used in step S11 to detect serotonin in the culture medium or the sample thereof and determine the concentration of the detected serotonin. In this optional embodiment, the ratio or quotient is calculated in step S12 only if the concentration of detected in step S11 in the culture medium when cultured under anaerobic conditions is equal to or above this threshold value.

If the lactic acid producing bacterial strain is capable of producing and releasing serotonin when cultured in aerobic conditions but not when cultured in anaerobic conditions, the lactic acid producing bacterial strain could still be selected in step S3 as effective in treating serotonin deficiency and/or the disease related to serotonin deficiency in the subject according to the embodiment shown in FIG. 6 if the concentration of serotonin in the supernatant is at least 0.4 nM, preferably at least 0.5 nM, such as at least 0.75 nM or at least 1 nM, preferably at least 2 nM, more preferably at least 3 nM, such as at least 4 nM, or at least 5 nM or at least 6 nM or at least 7 nM as is further mentioned below.

This embodiment of the invention thereby selects lactic acid bacterial strains that are in particular good serotonin producers in aerobic conditions, i.e., produce at least as much, preferably more, serotonin under aerobic conditions as compared to under anaerobic conditions. Most lactic acid producing bacterial strains are anaerobic, some of which may produce serotonin under anaerobic conditions. However, the present invention selects lactic acid bacterial strains that not only can survive and grow in aerobic conditions but may also produce and extracellularly release serotonin under such aerobic condition. Furthermore, the lactic acid bacterial strains selected in accordance with the embodiment as shown in FIG. 6 in fact produces at least as much, if not more, serotonin under the aerobic condition as compared to the anaerobic condition. Such lactic acid bacterial strains may produce and secrete biologically effective quantities of serotonin when present in niches of the gastrointestinal system or tract of a subject where oxygen levels are relatively higher than in other parts of the gastrointestinal tract and are therefore in particular suitable for use in treatment of serotonin deficiency and/or a disease related to serotonin deficiency.

In an embodiment, step S2 in FIG. 5 comprises measuring a concentration of serotonin produced and released by the lactic acid producing bacterial strain in the culture medium or the sample thereof. Step S3 comprises, in this embodiment, selecting the lactic acid producing bacterial strain as effective in treating serotonin deficiency in the subject if the concentration of serotonin in the culture medium or the sample thereof is at least equal to or above a defined threshold value.

The concentration of serotonin as measured in the culture medium or the sample thereof for a given lactic acid producing bacterial strain is at least partly dependent on the assay or technology used for analyzing serotonin, such as ELISA versus MS. Hence, the value of the threshold value as mentioned above is dependent on the particular assay used to measure the concentration of serotonin in the culture medium.

In a particular embodiment, bacteria of the lactic acid producing bacterial strain are cultured for 24 hours under aerobic conditions in the tryptophan comprising culture medium, preferably the DECT culture medium, followed by taking a culture medium sample and subjecting the culture medium sample to at least one centrifugation to obtain a supernatant and a pellet. In such a case, the concentration of serotonin produced by the bacteria lactic acid producing bacterial strain is measured in the supernatant using a regular mass spectrometry assay. In this particular embodiment, step S3 comprises selecting the lactic acid producing bacterial strain as effective in treating serotonin deficiency and/or the disease related to serotonin deficiency in the subject if the concentration of serotonin in the supernatant is at least 0.4 nM, preferably at least 0.5 nM, such as at least 0.75 nM or at least 1 nM, preferably at least 2 nM, more preferably at least 3 nM, such as at least 4 nM, or at least 5 nM or at least 6 nM or at least 7 nM.

Figure 7:
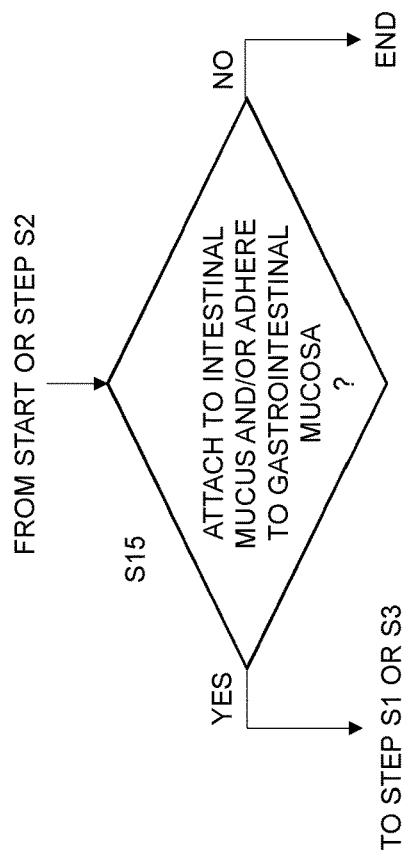
FIG. 7 is a flow chart illustrating an additional, optional step to the method shown in FIG. 5 according to an embodiment.

In an embodiment, the method comprises an additional step S15 as shown in FIG. 7. The method starts in this step S15 or continues from step S2 in FIG. 5, or indeed from step S13 in FIG. 6. Step S15 comprises determining whether the bacteria of the lactic acid producing bacterial strain are capable of attaching to intestinal mucus and/or are capable of adhering to a gastrointestinal mucosa. In this embodiment, step S3 in FIG. 5 comprises selecting the lactic acid producing bacterial strain as effective in treating serotonin deficiency and/or the disease related to serotonin deficiency in a subject if serotonin is detected in the culture medium or the sample thereof and if the bacteria of the lactic acid producing bacterial strain are capable of attaching to intestinal mucus and/or are capable of adhering to the gastrointestinal mucosa.

This embodiment may also be combined with the embodiment as shown in FIG. 6, i.e., performing the selection based on the comparison of the ratio and threshold value and based on whether the bacteria of the lactic acid producing bacterial strain are capable of attaching to intestinal mucus and/or are capable of adhering to the gastrointestinal mucosa.

Mucus with its main structural components mucins (a family of high molecular weight, heavily glycosylated proteins) is produced by mucous membranes in mammals and birds, and also in amphibians, fish, hagfish, snails and slugs. Hence, by being capable of attaching to intestinal mucus, bacteria of the lactic acid producing bacterial strain can attach to the mucosa of the gastrointestinal tract.

The capability of bacteria of a lactic acid producing bacterial strain to attach to the mucosa of the gastrointestinal tract can be investigated, for instance, as disclosed in Example 6. In brief, gastrointestinal mucosa is extracted and plated on a surface. Bacteria of the lactic acid producing bacterial strain are then added to the plated mucus and allowed to adhere to the mucus. Non-binding bacteria are then removed by one or multiple washes. The amount of adhering bacteria can then be quantified directly on the mucus, or indirect by first releasing the adhering bacteria, such as through enzyme treatment, for instance trypsin treatment, and then quantifying the released bacteria.

In an embodiment, the lactic acid producing bacterial strain has a mucus adhesion that is at least as good as the mucus adhesion capability of *Lactobacillus reuteri* DSM 27131, such as shown in Example 6. In such an embodiment, step S15 in FIG. 7 comprises determining whether the bacteria of the lactic acid producing bacterial strain has a mucus adhesion capability equal to or higher than a mucus adhesion capability of bacteria of *L. reuteri* DSM 27131. In this embodiment, step S3 in FIG. 5 comprises selecting the lactic acid producing bacterial strain as effective in treating serotonin deficiency and/or the disease related to serotonin deficiency in a subject if serotonin is detected in the culture medium or the sample thereof and if the bacteria of the lactic acid producing bacterial strain has a mucus adhesion capability equal to or higher than the mucus adhesion capability of bacteria of *L. reuteri* DSM 27131.

The above described method and embodiments thereof is an in vitro method for identification and selection of lactic acid producing bacteria as effective in treating serotonin deficiency and/or the disease related to serotonin deficiency in a subject.

Figure 8:
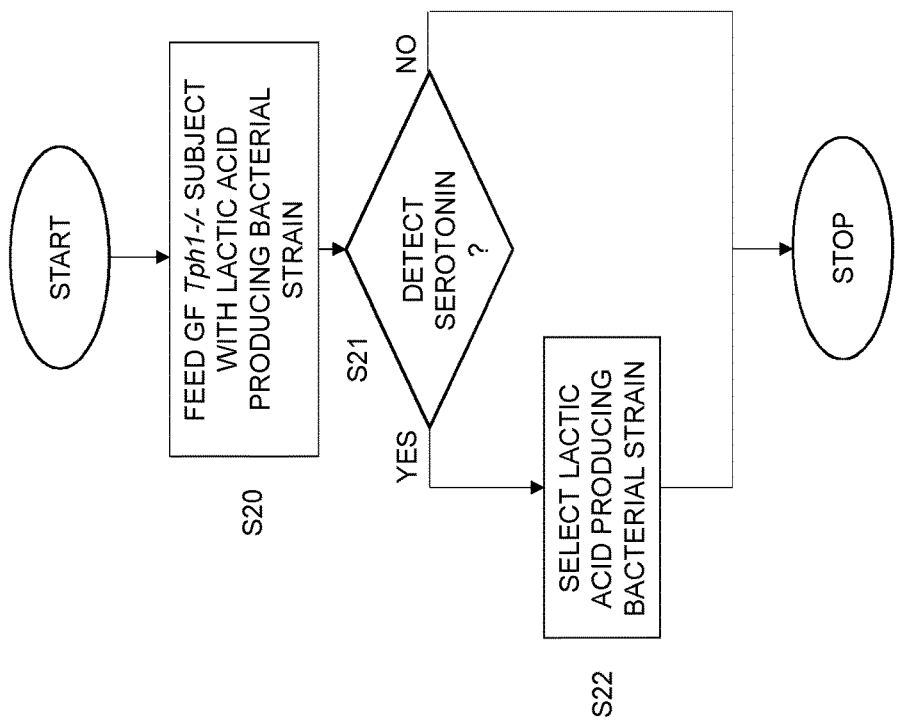
FIG. 8 is a flow chart illustrating a method for selecting a bacterial strain according to another embodiment.

The invention is, however, not limited thereto. FIG. 8 is a flow chart illustrating a method for selecting a bacterial strain for use in treating serotonin deficiency and/or a disease related serotonin deficiency that is conducted as an in vivo method. The method comprises feeding, i.e., inoculating, a germ free (GR) Tph1−/− subject with bacteria of a lactic acid producing bacterial strain in step S20. A next step S21 comprises detecting any serotonin produced by the bacteria of the lactic acid producing bacterial strain a body sample taken from the GF Tph1−/− subject. The method further comprises selecting, in step S22, the lactic acid producing bacterial strain as effective in treating serotonin deficiency and/or a disease related serotonin deficiency in a subject if serotonin is detected in the body sample. Hence, in this method a test subject in terms of a germ free test subject that lacks production of the enzyme TPH1, i.e., is a Tph1 knockout subject. The GF Tph1−/− subject is a non-human GF Tph1−/− animal subject and preferably selected from the group consisting of mouse, rat, guinea pig, pig, cat, dog, sheep, horse, non-human primate, monkey or bird, and more preferably mouse or rat. GF Tph1−/− mice can be obtained as disclosed in Example 1.

The bacteria of the lactic acid producing bacterial strain to be tested in the method shown in FIG. 8 are fed, i.e., inoculated, such as gavaged, to the GF Tph1−/− subject, such as in the form of a solubilized powder, capsule, or tablet comprising the bacteria or a solution comprising the bacteria. A body sample is taken from the GF Tph1−/− subject and analyzed in step S21 for the presence of any serotonin. The subject is germ free, i.e., lacks or deficient of gastrointestinal microbiota, and in addition lacks TPH1, which is the enzyme responsible for most of the endogenous serotonin production. Hence, any serotonin detected in the body sample in step S21 is produced by bacteria of the lactic acid producing bacterial strain fed to the subject in step S20, or bacteria obtained from the inoculated bacteria.

The body sample could be any sample taken from the GF Tph1−/− subject and that would normally contain serotonin if the subject was not Tph1−/−, i.e., a non-GF Tph1+/+ subject of the same species. For instance, the sample could be a gastrointestinal sample, a tissue sample taken from the subject, such as from gastrointestinal tissue, or a body fluid sample, such as a blood sample, a plasma sample or a serum sample. In a particular embodiment, the body sample is a body fluid sample, preferably a blood sample, a plasma sample or serum sample. Serotonin detected in such a body fluid sample not only indicates that the bacteria of the lactic acid producing bacterial strain are capable of producing and extracellularly producing serotonin in the gastrointestinal system of the GF Tph1−/− subject but also that the bacterially produced serotonin is taken up and transported into the systemic circulation, i.e., blood system, of the GF Tph1−/− subject.

In an embodiment, the lactic acid producing bacterial strain is a *Lactobacillus* bacterial strain. In a particular embodiment, the *Lactobacillus* bacterial strain is selected from the group consisting of a *L. reuteri* bacterial strain, a *L. mucosae* bacterial strain, and a *L. plantarum* bacterial strain.

In an embodiment, the lactic acid producing bacterial strain selected according the invention, such as shown in any of FIGS. 5 to 8, are not only capable of producing and extracellularly releasing serotonin but also capable of inducing endogenous serotonin production when administered to a subject.

In another embodiment, the lactic acid producing bacterial strain selected according the invention, such as shown in any of FIGS. 5 to 8, are capable of producing and extracellularly releasing serotonin but not capable of inducing endogenous serotonin production when administered to a subject.

Another aspect of the invention relates to a lactic acid producing bacterial strain capable of producing and extracellularly releasing serotonin under aerobic conditions for use in treatment of serotonin deficiency and/or a disease related to serotonin deficiency in a subject.

In an embodiment, the lactic acid producing bacterial strain is also capable of producing and extracellularly releasing serotonin under anaerobic conditions but a ratio between an amount of serotonin produced and extracellularly produced by bacteria of the lactic acid producing bacterial strain under aerobic conditions and an amount of serotonin produced and extracellularly produced by bacteria of the lactic acid producing bacterial strain under anaerobic conditions is equal to or larger than one, preferably larger than one.

In an embodiment, the lactic acid producing bacterial strain is further capable of attaching to intestinal mucus and/or capable of adhering to a gastrointestinal mucosa.

In an embodiment, the lactic acid producing bacterial strain is capable of producing serotonin in, or at least in connection with, the intestinal mucosa of a subject.

As previously described herein, it is generally preferred if the bacteria of the lactic acid producing bacterial strain is capable of attaching to mucus or at least being present close to the gastrointestinal mucosa, and in particular the intestinal mucosa, to thereby promote uptake of the serotonin produced and secreted by the bacteria of the lactic acid producing bacterial strain by the intestinal mucosa, and in particular by the intestinal epithelium. The serotonin taken up by the intestinal epithelium can then be transported peripherally or systemically to the particular location in the subject where the serotonin is to exert its biological effect.

Herein, the term "treatment" may encompass both the alleviation of symptoms of a particular medical condition, disease or disorder as well as preventing the onset of symptoms. Accordingly, this term includes prevention, reducing the risk, reduction, inhibition and prophylaxis of serotonin deficiency and/or the disease related to serotonin deficiency.

In an embodiment, the lactic acid producing bacterial strain capable of producing serotonin under aerobic conditions is selected according to above described and in any of FIGS. 5 to 8 shown methods or embodiments thereof.

Serotonin has several physiological functions including behavior, platelet activation and coagulation, regulating gut motility and enteric nervous system (ENS) homeostasis and activity, intestinal immune system activity, energetic metabolism (fasting adaptation, browning and lipolysis of adipose tissue, hepatic glucose production, insulin secretion), gut-brain axis activity and bone metabolism and homeostasis. Hence, imbalance, and in particular deficiency, in serotonin levels can cause abnormalities in many biological processes and functions in a subject.

In an embodiment, a disease related to serotonin deficiency, also referred to as serotonin-dependent disease herein, is a disease or disorder selected from the group consisting of anxiety, depressed mood, aggression, poor memory, eating disorders, obsessive-compulsive disorder, panic disorder, post-traumatic stress disorder, social anxiety disorder, gastrointestinal motility disorder (such as constipation), irritable bowel syndrome (IBS), inflammatory bowel disease (IBD), a cardiovascular disease, osteoporosis, autoimmune polyendocrinopathy-candidiasis-ectodermal dystrophy (APECED), osteopenia, a bone loss condition, and a combination thereof.

In an embodiment, the disease related to serotonin deficiency is selected from the group consisting of IBS, IBD, a cardiovascular disease, osteoporosis, gastrointestinal motility disorder, APECED, osteopenia and a bone loss condition.

In an embodiment, the disease related to serotonin deficiency is a disease or disorder of the central nervous system, such as selected from the group consisting of anxiety, depressed mood, aggression, poor memory, eating disorders, obsessive-compulsive disorder, panic disorder, post-traumatic stress disorder, and social anxiety disorder.

In a preferred embodiment, the disease related to serotonin deficiency is a disease or disorder of the gastrointestinal system, such as a gastrointestinal motility disorder, IBS or IBD.

In an embodiment, the disease related to serotonin deficiency is a disease related to osteoporosis, osteopenia and bone loss conditions, such as glucocorticoid-associated bone loss.

In an embodiment, the lactic acid producing bacterial strain is a *Lactobacillus* bacterial strain. In a particular embodiment, the *Lactobacillus* bacterial strain is selected from a group consisting of a *L. reuteri* strain, a *L. mucosae* strain and a *L. plantarum* strain.

In an embodiment, the *L. reuteri* strain is selected from the group consisting of *L. reuteri* DSM 32846, *L. reuteri* DSM 32848, *L. reuteri* DSM 32849, *L. reuteri* DSM 27131, *L. reuteri* DSM 33509, *L. reuteri* DSM 33632, *L. reuteri* DSM 33633, *L. reuteri* DSM 33634, *L. reuteri* DSM 33635, *L. reuteri* ATCC PTA 5289, *L. reuteri* DSM 17938, *L. reuteri* ATCC PTA 6475, and *L. reuteri* DSM 32465.

In a particular embodiment, the *L. reuteri* strain is selected from the group consisting of *L. reuteri* DSM 32846, *L. reuteri* DSM 32848, *L. reuteri* DSM 32849, *L. reuteri* DSM 27131, *L. reuteri* DSM 33509, *L. reuteri* DSM 33632, *L. reuteri* DSM 33633, *L. reuteri* DSM 33634, *L. reuteri* DSM 33635, *L. reuteri* ATCC PTA 5289 and *L. reuteri* DSM 32465.

In another particular embodiment, the *L. reuteri* strain is selected from the group consisting of *L. reuteri* DSM 32846, *L. reuteri* DSM 32848, *L. reuteri* DSM 32849, *L. reuteri* DSM 27131, *L. reuteri* DSM 33509, *L. reuteri* DSM 33632, *L. reuteri* DSM 33633, *L. reuteri* DSM 33634, *L. reuteri* DSM 33635, *L. reuteri* DSM 17938 and *L. reuteri* DSM 32465.

In a further embodiment, the *L. reuteri* strain is selected from the group consisting of *L. reuteri* DSM 32846, *L. reuteri* DSM 32848, *L. reuteri* DSM 32849, *L. reuteri* DSM 27131, *L. reuteri* DSM 33509, *L. reuteri* DSM 33632, *L.*

*reuteri* DSM 33633, *L. reuteri* DSM 33634, *L. reuteri* DSM 33635, *L. reuteri* ATCC PTA 6475 and *L. reuteri* DSM 32465.

*Lactobacillus reuteri* DSM 27131 was deposited under the Budapest Treaty at the Leibniz Institut DSMZ-Deutsche Sammlung von Mikroorganismen und Zellkulturen GmbH (Inhoffenstr. 7B, D-38124 Braunschweig, Germany) on Apr. 18, 2013.

*Lactobacillus reuteri* DSM 32846, DSM 32848 and DSM 32849 were deposited under the Budapest Treaty at the Leibniz Institut DSMZ-Deutsche Sammlung von Mikroorganismen und Zellkulturen GmbH (Inhoffenstr. 7B, D-38124 Braunschweig, Germany) on Jul. 4, 2018.

*Lactobacillus reuteri* DSM 33509 was deposited under the Budapest Treaty at the Leibniz Institut DSMZ-Deutsche Sammlung von Mikroorganismen und Zellkulturen GmbH (Inhoffenstr. 7B, D-38124 Braunschweig, Germany) on Apr. 23, 2020.

*Lactobacillus reuteri* DSM 32465 was deposited under the Budapest Treaty at the Leibniz Institute DSMZ-German collection of Microorganisms and Cell Cultures (Inhoffenstr. 7B, D-38124 Braunschweig, Germany) on Mar. 21, 2017.

*Lactobacillus reuteri* ATCC PTA 5289 was deposited under the Budapest Treaty at the American Type Culture Collection (10801 University Blvd., Manassas, VA 20110-2209, U.S.) on Jun. 25, 2003.

*Lactobacillus reuteri* DSM 33632, DSM 33633, DSM 33634, and DSM 33635 were deposited under the Budapest Treaty at the Leibniz Institut DSMZ-Deutsche Sammlung von Mikroorganismen und Zellkulturen GmbH (Inhoffenstr. 7B, D-38124 Braunschweig, Germany) on Sep. 9, 2020.

*Lactobacillus reuteri* DSM 17938 was deposited under the Budapest Treaty at the DSMZ-Deutsche Sammlung von Mikroorganismen und Zellkulturen GmbH (Mascheroder Weg 1b, D-38124 Braunschweig, Germany) on Jan. 30, 2006.

*Lactobacillus reuteri* ATCC PTA 6475 was deposited under the Budapest Treaty at the American Type Culture Collection (10801 University Blvd., Manassas, VA 20110-2209, U.S.) on Dec. 21, 2004.

In a particular embodiment, the *L. reuteri* strain is selected from the group consisting of *L. reuteri* DSM 32846, *L. reuteri* DSM 32848, *L. reuteri* DSM 32849, *L. reuteri* DSM 27131, *L. reuteri* DSM 33509, *L. reuteri* DSM 33632, *L. reuteri* DSM 33633, *L. reuteri* DSM 33634, *L. reuteri* DSM 33635, and *L. reuteri* DSM 32465.

In another particular embodiment, the *L. reuteri* strain is selected from the group consisting of *L. reuteri* DSM 33632, *L. reuteri* DSM 33633, *L. reuteri* DSM 33634, *L. reuteri* DSM 33635, and *L. reuteri* DSM 33509.

In a further particular embodiment, the *L. reuteri* strain is selected from the group consisting of *L. reuteri* DSM 33632, *L. reuteri* DSM 33633, *L. reuteri* DSM 33634, and *L. reuteri* DSM 33635. These *L. reuteri* strains have been evolved to be more oxygen tolerant and to be stable and viable for prolonged periods of storage as described below.

Figure 9B:
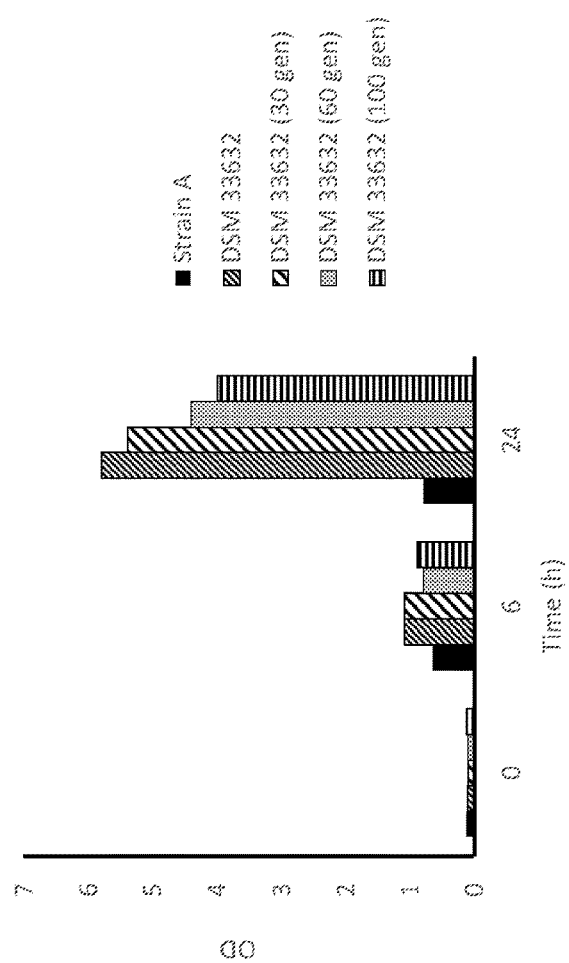
FIG. 9. Two *Lactobacillus reuteri* strains that do not grow well under aerobic conditions, strain A and strain B, were challenged by oxygen during culture to evolve into new, more oxygen tolerant strains. Two new strains, *L. reuteri* DSM 33632 and DSM 33634, originating from strain A and strain B, respectively, were identified by this method. Growth by the bacterial strains was quantified by measurement of optical density (OD) at 24 hours of culture, and both new strains had significantly improved OD under aerobic conditions as compared to the strains (A). This improved growth was stable for up to 100 generations (B, C). The new, more oxygen tolerant, bacterial strains were further challenged by several more rounds of oxygen stress to further evolve into additional, even more oxygen tolerant strains, and also with an additional freeze-drying step and an accelerated storage stress. These additional stress steps led to the identification and selection of two additional new bacterial strains, *L. reuteri* DSM 33633, originating from DSM 33632, and *L. reuteri* DSM 33635, originating from DSM 33634. These two new strains displayed slightly improved growth characteristics under aerobic conditions as compared to DSM 33632 and DSM 33634, as well as significantly improved growth properties under aerobic conditions as compared to strain A and strain B (D).
Figure 9A:
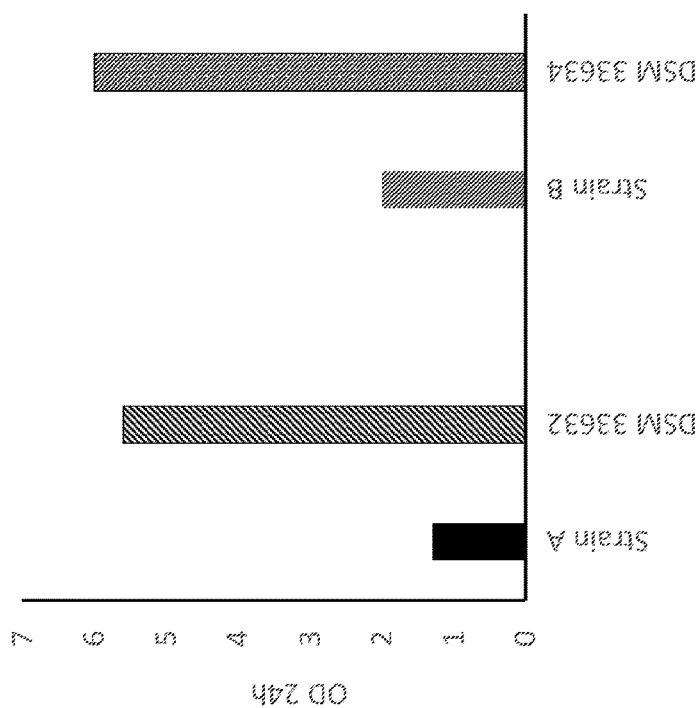
Figure 9D:
Figure 9C:
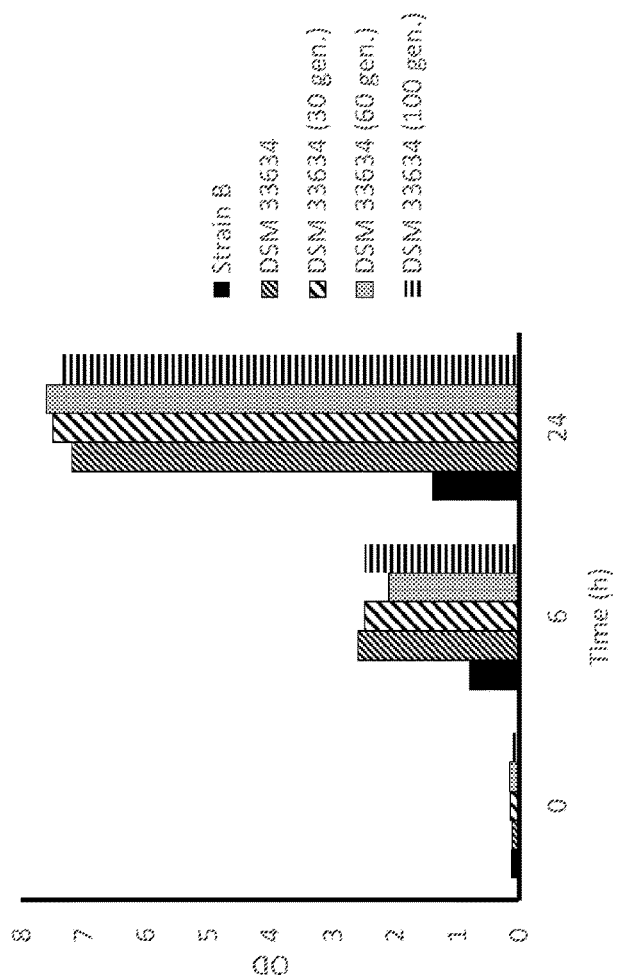

Several *Lactobacillus* strains grow well under anaerobic, but not under aerobic conditions. Therefore, two *L. reuteri* strains with poor oxygen tolerance, strain A and strain B, were challenged by oxygen (oxygen stress) and were thereby forced in a laboratory-controlled environment to evolve, i.e., they were actively modified or adapted, into new strains. Two new strains were identified by this method, *L. reuteri* DSM 33632 was identified originating from parent strain A and *L. reuteri* DSM 33634 was identified originating from parent strain B. Both these new strains displayed newly developed and improved properties, one of these being increased oxygen tolerance, which made them grow significantly better under aerobic conditions (FIG. 9A) for up to 100 generations (FIGS. 9B and 9C).

Furthermore, there is a general need to improve the storage stability of bacterial cultures for use in probiotic products, which includes both making the bacteria more tolerant to a freeze-drying process and more stable during long-term storage to increase the shelf-life of the probiotic product. Therefore, the new more oxygen tolerant bacterial strains were further challenged in a laboratory-controlled environment including several more rounds of oxygen stress to make them even more tolerant to aerobic conditions, as well as with an additional freeze-drying and an accelerated storage stress, which led to the identification and selection of an additional two bacterial strains, *L. reuteri* DSM 33633 originating from DSM 33632 and *L. reuteri* DSM 33635 originating from DSM 33634. These additional two new strains not only withstood the additional freeze-drying steps and accelerated storage stress, but also displayed slightly improved growth characteristics under aerobic conditions as compared to DSM 33632 and DSM 33634 (FIG. 9D) and significantly improved growth properties under aerobic conditions as compared to parent strain A and parent strain B. All four of the modified strains, *L. reuteri* DSM 33632, DSM 33633, DSM 33634, and DSM 33635, displayed these adapted/evolved properties, which were found to remain stable for at least 100 generations.

In a particular embodiment, the *L. reuteri* strain is *L. reuteri* DSM 33509. This *L. reuteri* strain was challenged to evolve into a more stable bacterial strain with the aim of increasing viability for prolonged periods of storage and also to improve survival in the gastrointestinal tract. In more detail, the *L. reuteri* strain DSM 33509 has been modified from its parent strain in a multi-step selection process, which involved cultivating and lyophilising the bacteria and selection of colonies that survived the lyophilisation step which resulted in a strain with increased resistance to bile and increased adhesion to MUCUS.

In an embodiment, the *L. mucosae* strain is selected from the group consisting of *L. mucosae* DSM 33291, *L. mucosae* DSM 33292, *L. mucosae* DSM 33293 and *L. mucosae* DSM 33661.

*L. mucosae* DSM 33291, DSM 33292 and DSM 33293 were deposited under the Budapest Treaty at the Leibniz Institute DSMZ-German Collection of Microorganisms and Cell Cultures (Inhoffenstr. 7B, D-38124 Braunschweig, Germany) on Sep. 20, 2019.

*L. mucosae* DSM 33661 was deposited under the Budapest Treaty at the Leibniz Institute DSMZ-German Collection of Microorganisms and Cell Cultures (Inhoffenstr. 7B, D-38124 Braunschweig, Germany) on Oct. 14, 2020.

In an embodiment, the *L. plantarum* strain is selected from the group consisting of *L. plantarum* DSM 33295 and *L. plantarum* DSM 33662,

*L. plantarum* DSM 33295 was deposited under the Budapest Treaty at the Leibniz Institute DSMZ-German Collection of Microorganisms and Cell Cultures (Inhoffenstr. 7B, D-38124 Braunschweig, Germany) on Oct. 9, 2019.

*L. plantarum* DSM 33662 was deposited under the Budapest Treaty at the Leibniz Institute DSMZ-German Collection of Microorganisms and Cell Cultures (Inhoffenstr. 7B, D-38124 Braunschweig, Germany) on Oct. 14, 2020.

In a particular embodiment, the lactic acid bacterial strain is selected from the group consisting of *L. reuteri* DSM 33632, *L. reuteri* DSM 33633, *L. reuteri* DSM 33634, *L. reuteri* DSM 33635, and *L. reuteri* DSM 33509, *L. mucosae* DSM 33291, *L. mucosae* DSM 33292, *L. mucosae* DSM 33293, *L. mucosae* DSM 33661, *L. plantarum* DSM 33295, and *L. plantarum* DSM 33662.

It is also possible to use a combination of bacteria from two or more lactic acid producing bacterial strains, such as selected from the above presented *L. mucuosae, L. plantarum* and *L. reuteri* strains.

In an embodiment the lactic acid producing bacterial strains are preferably probiotic bacterial strains.

In an embodiment, the lactic acid producing bacterial strain is other than *Lactobacillus reuteri* DSM 17938 when the disease related to serotonin deficiency is selected from the group consisting of IBS, anxiety, depressed mood, post-traumatic stress disorder, IBD and gastrointestinal motility disorders. In another embodiment, the lactic acid producing bacterial strain is other than *Lactobacillus reuteri* DSM 17938.

In an embodiment, the lactic acid producing bacterial strain is other than *Lactobacillus reuteri* ATCC PTA 6475 when the disease related to serotonin deficiency is selected from the group consisting of osteoporosis, osteopenia, bone loss, depressed mode, IBS and IBD. In another embodiment, the lactic acid producing bacterial strain is other than *Lactobacillus reuteri* ATCC PTA 6475.

Further embodiments of the invention relates to *Lactobacillus mucosae* strain DSM 33291, such as *L. mucosae* strain DSM 33291 in lyophilized or otherwise dried form, *L. mucosae* strain DSM 33291 for use as a medicament, *L. mucosae* strain DSM 33291 for use in treatment of serotonin deficiency and/or a disease related to serotonin deficiency and use of *L. mucosae* strain DSM 33291 for the manufacture of a medicament for the treatment of serotonin deficiency and/or a disease related to serotonin deficiency.

Additional embodiments of the invention relates to *Lactobacillus mucosae* strain DSM 33292, such as *L. mucosae* strain DSM 33292 in lyophilized or otherwise dried form, *L. mucosae* strain DSM 33292 for use as a medicament, *L. mucosae* strain DSM 33292 for use in treatment of serotonin deficiency and/or a disease related to serotonin deficiency and use of *L. mucosae* strain DSM 33292 for the manufacture of a medicament for the treatment of serotonin deficiency and/or a disease related to serotonin deficiency.

Embodiments of the invention further relates to *Lactobacillus mucosae* strain DSM 33293, such as *L. mucosae* strain DSM 33293 in lyophilized or otherwise dried form, *L. mucosae* strain DSM 33293 for use as a medicament, and *L. mucosae* strain DSM 33293 for use in treatment of serotonin deficiency and/or a disease related to serotonin deficiency and use of *L. mucosae* strain DSM 33293 for the manufacture of a medicament for the treatment of serotonin deficiency and/or a disease related to serotonin deficiency.

Embodiments of the invention also relate to *Lactobacillus mucosae* strain DSM 33661, such as *L. mucosae* strain DSM 33661 in lyophilized or otherwise dried form, *L. mucosae* strain DSM 33661 for use as a medicament, and *L. mucosae* strain DSM 33661 for use in treatment of serotonin deficiency and/or a disease related to serotonin deficiency and use of *L. mucosae* strain DSM 33661 for the manufacture of a medicament for the treatment of serotonin deficiency and/or a disease related to serotonin deficiency.

Further embodiments of the invention relate to *Lactobacillus plantarum* strain DSM 33295, such as *L. plantarum* strain DSM 33295 in lyophilized or otherwise dried form, *L. plantarum* strain DSM 33295 for use as a medicament, *L. plantarum* strain DSM 33295 for use in treatment of serotonin deficiency and/or a disease related to serotonin deficiency and use of *L. plantarum* strain DSM 33295 for the manufacture of a medicament for the treatment of serotonin deficiency and/or a disease related to serotonin deficiency.

Embodiments of the invention further relate to *Lactobacillus plantarum* strain DSM 33662, such as *L. plantarum* strain DSM 33662 in lyophilized or otherwise dried form, *L. plantarum* strain DSM 33662 for use as a medicament, *L. plantarum* strain DSM 33662 for use in treatment of serotonin deficiency and/or a disease related to serotonin deficiency and use of *L. plantarum* strain DSM 33662 for the manufacture of a medicament for the treatment of serotonin deficiency and/or a disease related to serotonin deficiency.

Additional embodiments of the invention relate to *Lactobacillus reuteri* strain DSM 33509, such as *L. reuteri* strain DSM 33509 in lyophilized or otherwise dried form, *L. reuteri* strain DSM 33509 for use as a medicament, *L. reuteri* strain DSM 33509 for use in treatment of serotonin deficiency and/or a disease related to serotonin deficiency and use of *L. reuteri* strain DSM 33509 for the manufacture of a medicament for the treatment of serotonin deficiency and/or a disease related to serotonin deficiency.

Embodiments of the invention relate to *Lactobacillus reuteri* strain DSM 33632, such as *L. reuteri* strain DSM 33632 in lyophilized or otherwise dried form, *L. reuteri* strain DSM 33632 for use as a medicament, *L. reuteri* strain DSM 33632 for use in treatment of serotonin deficiency and/or a disease related to serotonin deficiency and use of *L. reuteri* strain DSM 33632 for the manufacture of a medicament for the treatment of serotonin deficiency and/or a disease related to serotonin deficiency.

Embodiments of the invention also relate to *Lactobacillus reuteri* strain DSM 33633, such as *L. reuteri* strain DSM 33633 in lyophilized or otherwise dried form, *L. reuteri* strain DSM 33633 for use as a medicament, *L. reuteri* strain DSM 33633 for use in treatment of serotonin deficiency and/or a disease related to serotonin deficiency and use of *L. reuteri* strain DSM 33633 for the manufacture of a medicament for the treatment of serotonin deficiency and/or a disease related to serotonin deficiency.

Further embodiments of the invention relate to *Lactobacillus reuteri* strain DSM 33634, such as *L. reuteri* strain DSM 33634 in lyophilized or otherwise dried form, *L. reuteri* strain DSM 33634 for use as a medicament, *L. reuteri* strain DSM 33634 for use in treatment of serotonin deficiency and/or a disease related to serotonin deficiency and use of *L. reuteri* strain DSM 33634 for the manufacture of a medicament for the treatment of serotonin deficiency and/or a disease related to serotonin deficiency.

Additional embodiments of the invention relate to *Lactobacillus reuteri* strain DSM 33635, such as *L. reuteri* strain DSM 33635 in lyophilized or otherwise dried form, *L. reuteri* strain DSM 33635 for use as a medicament, *L. reuteri* strain DSM 33635 for use in treatment of serotonin deficiency and/or a disease related to serotonin deficiency and use of *L. reuteri* strain DSM 33635 for the manufacture of a medicament for the treatment of serotonin deficiency and/or a disease related to serotonin deficiency.

The present invention, thus, relates to a lactic acid producing bacterial strain selected from the group consisting of *Lactobacillus mucosae* DSM 33291, *L. mucosae* DSM 33292, *L. mucosae* DSM 33293, *L. mucosae* DSM 33661, *L. plantarum* DSM 33295, *L. plantarum* DSM 33662, *L. reuteri* DSM 33509, *L. reuteri* DSM 33632, *L. reuteri* DSM 33633, *L. reuteri* DSM 33634, and *L. reuteri* DSM 33635, such as in lyophilized or otherwise dried form. The present invention also relates to a lactic acid producing bacterial selected from the above mentioned group for use as a medicament, for use in treatment of serotonin deficiency and/or a disease related to serotonin deficiency, and use thereof for the manufacture of a medicament for the treatment of serotonin deficiency and/or a disease related to serotonin deficiency.

An aspect of the invention relates to a bacterial strain that produces and extracellularly releases serotonin under aerobic conditions. In an embodiment, the bacterial strain is selected from the group consisting of *Lactobacillus mucosae* DSM 33291, *L. mucosae* DSM 33292, *L. mucosae* DSM 33293, *L. mucosae* DSM 33661, *L. plantarum* DSM 33295, *L. plantarum* DSM 33662, *L. reuteri* DSM 33509, *L. reuteri* DSM 33632, *L. reuteri* DSM 33633, *L. reuteri* DSM 33634, and *L. reuteri* DSM 33635.

In a particular embodiment, the bacterial strain is a *Lactobacillus mucosae* strain selected from the group consisting of *L. mucosae* DSM 33291, *L. mucosae* DSM 33292, *L. mucosae* DSM 33293, and *L. mucosae* DSM 33661.

In another particular embodiment, the bacterial strain is a *Lactobacillus plantarum* strain selected from the group consisting of *L. plantarum* DSM 33295, and *L. plantarum* DSM 33662.

In a further particular embodiment, the bacterial strain is a *Lactobacillus reuteri* strain selected from the group consisting of *L. reuteri* DSM 33509, *L. reuteri* DSM 33632, *L. reuteri* DSM 33633, *L. reuteri* DSM 33634, and *L. reuteri* DSM 33635.

Another aspect of the invention relates to a bacterial strain that produces and extracellularly releases serotonin under aerobic conditions and is capable of attaching to mucus. In an embodiment, the bacterial strain is selected from the group consisting of *Lactobacillus mucosae* DSM 33291, *L. mucosae* DSM 33292, *L. mucosae* DSM 33293, *L. mucosae* DSM 33661, *L. plantarum* DSM 33662, *L. reuteri* DSM 33509, *L. reuteri* DSM 33632, *L. reuteri* DSM 33633, *L. reuteri* DSM 33634 and *L. reuteri* DSM 33635.

In a particular embodiment, the bacterial strain is a *Lactobacillus mucosae* strain selected from the group consisting of *L. mucosae* DSM 33291, *L. mucosae* DSM 33292, *L. mucosae* DSM 33293, and *L. mucosae* DSM 33661.

In another particular embodiment, the bacterial strain is a *Lactobacillus plantarum* DSM 33662.

In a further particular embodiment, the bacterial strain is a *Lactobacillus reuteri* strain selected from the group consisting of *L. reuteri* DSM 33509, *L. reuteri* DSM 33632, *L. reuteri* DSM 33633, *L. reuteri* DSM 33634, and *L. reuteri* DSM 33635.

A preferred mode of administration of the lactic acid producing bacterial strains is oral. Other modes of administration include nasal, intraocular, topical or some other form of local administration to the skin, rectum, nose, eyes, vagina or gums.

Appropriate doses of the lactic acid producing bacterial strains as defined herein can readily be chosen depending on the disease related to serotonin deficiency to be treated, the mode of administration, the subject and the formulation concerned. For example, a dosage and administration regime are chosen such that the lactic acid producing bacteria administered to the subject in accordance with the present invention can result in desired therapeutic effects, prophylactic effects or health benefits. Thus, preferably the dosage is a therapeutically or prophylactically effective dosage, which is appropriate for the type of mammal and serotonin deficiency being treated. For example, daily doses of $10^4$ to $10^{11}$, for example $10^5$ to $10^9$, or $10^6$ to $10^8$, or $10^8$ to $10^{10}$ total colony forming units (CFUs) of bacteria may be used. A preferred daily dose is around $10^8$ total CFUs, e.g., $10^7$ to $10^9$ or $10^8$ to $10^9$ CFUs. The lactic acid producing bacterial strain is preferably administered in a pure, isolated, dried, lyophilized or freeze-dried form. The lactic acid producing bacteria can also be administered in a frozen or active formulation (e.g., in a fermented food product). Hence, the lactic acid producing bacterial strain is preferably produced or prepared in a lyophilized or freeze-dried form.

The lactic acid producing bacterial strain, preferably in a lyophilized form, may be comprised in a composition comprising, in addition to the lactic acid producing bacterial strain, at least one excipient and/or other active agent. Non-limiting, but illustrative, examples of such excipients include fillers, anti-adherents, binders, coatings, colors, disintegrants, flavors, glidants, lubricants, preservatives, sorbents, sweeteners and vehicles.

Other active agents that could be comprised in the composition include such active agents that are used for treatment of any of the above-mentioned examples of serotonin deficiency diseases or disorders.

A related aspect of the invention defines a method of preventing, inhibiting or treating serotonin deficiency and/or a disease related to serotonin deficiency in a subject. The method comprises administering bacteria of a lactic acid producing bacterial strain capable of producing and extracellularly releasing serotonin under aerobic conditions to the subject.

Any of the above described administration routes could be used. The lactic acid producing bacterial strain may advantageously be administered in the form of a composition as described above.

The subject to be treated with the lactic acid producing bacterial strain or composition is a mammal or bird, and preferably a human. The lactic acid producing bacterial strain or composition could, however, also or alternatively be used for veterinary purposes. In such a case, the subject could, for instance, be selected among cats, dogs, sheep, goats, cows, horses as illustrative, but non-limiting, examples.

EXAMPLES

The gut microbiota produces a wide range of metabolites that impact host physiology, such as secondary bile acids and short-chain fatty acids. However, the microbiota has a vast and relatively unexplored potential for the transformation of aromatic amino acids. The present Examples demonstrate that serotonin produced in the lumen by gut microbes, such as *Lactobacillus*, is absorbed and have effects both locally and peripherally. The microbially produced serotonin is bioactive and can rescue developmental phenotypes of the enteric nervous system. The present Examples also show that specifically good serotonin producing bacteria can be isolated and selected for its ability to produce serotonin under aerobic conditions. Such serotonin producing bacteria has also been shown to be capable of producing serotonin in vivo.

Example 1—In Vitro and In Vivo Production of Serotonin and Assessment of Suitable Bacterial Strains Material and Methods
Animals 8-12-week-old Tph1+/+ (as littermate control) and Tph1−/− (C57Bl/6 background) mice were housed in a climate-controlled room (22±2° C.) subjected to a 12 h light/dark cycle (7:00 AM-7:00 PM), with free access to water and food. Tph1−/− mice were described previously (Cell 135: 825-837 (2008)). All animal procedures were approved by the Ethics Committee on Animal Care and Use in Gothenburg, Sweden. Animals were obtained from heterozygous breeding and were genotyped before experiments. The proximal colon, the serum from vena cava, material from the intestinal lumen and the caecum were obtained from each animal after the experiment. TPH1 is the rate-limiting enzyme involved in endogenous serotonin synthesis in the periphery including in the gastrointestinal tract. Tph1 knockout (Tph1−/−) mice are, thus, deficient in endogenous production of serotonin outside of the brain. The knockout of Tph1 expression in the Tph1−/− mouse gastrointestinal tract was confirmed by quantitative polymerase chain reaction (qPCR). Some very low levels of serotonin in these knockout animals remained even after re-deriving the animals as germ free (GF). It is possible that these low levels could have been produced by compensatory mechanisms, which are common in knockout animals, such as by non-specific hydroxylation of tryptophan by phenylalanine or tyrosine hydroxylases in the gut.

Bacterial Culture, Lactobacillus

For in vitro experiments, *Lactobacillus reuteri* (DSM 17938, DSM 32846, DSM 32848, DSM 32849, DSM 27131 and ATCC PTA 6475), *L. plantarum* 36E (obtained from the Culture Collection University of Gothenburg as "CCUG 61730"), *L. casei* LMG 6904 (obtained from the Belgian Coordinated Collections of Microorganisms) and *L. acidophilus* ATCC 4356 (obtained from the American Type Culture Collection) were cultured in tryptophan modified decarboxylase (DECT) broth under anaerobic condition, i.e., inside a Coy chamber. In parallel experiments, *Lactobacillus reuteri* strains (DSM 17938, DSM 32846, DSM 32848, DSM 32849, DSM 27131 and ATCC PTA 6475) were cultured in tryptophan modified DECT broth under ambient aerobic conditions. Each culture was sampled at 24 h and the samples were centrifuged (10,000×g, 4° C., 2 min). The pellets were collected and preserved in 20% glycerol (cryoprotectant) and frozen at −80° C. until use.

The tryptophan modified DECT broth was designed to promote tryptophan decarboxylation and production of serotonin by bacteria. DECT contained 0.5% beef extract (BD Biosciences #212303), 0.1% yeast extract (Oxoid Fisher-Scientific #LP0021), d-glucose 0.05% (Millipore #346351), L-tryptophan 1% (Sigma-Aldrich #93659) and, for anaerobic conditions, 0.05% cysteine in distilled water. To obtain anoxic varieties of DECT, cysteine 0.05%, was added as reducing agent. The DECT was autoclaved for 30 min, 15 PSI at 121° C.

Mouse Inoculation Experiments, Lactobacillus

For these experiments, bacterial strains *L. reuteri* (DSM 17938, DSM 27131) and *L. casei* (LMG 6904) were cultured as above under anaerobic conditions, but in De Man, Rogosa and Sharpe (MRS) medium instead of DECT broth. Culture samples were collected at 24 h, centrifuged (4500×g, 20 min, 4° C.), whereafter the supernatant was removed. The bacterial pellets were resuspended in a hungate tube containing 5 mL sterile reducing buffer (reduced and sterile PBS mixed with $Na_2S.9H_2O$ 0.24 g/L and cysteine 0.5 g/L in the presence of $NaHCO_3$ 4 g/L). Adult Tph1−/− mice were transferred into an experimental isolator and fasted during 4 h. The mice were then gavaged (fed, inoculated) with 200 μL of a solution containing either of the bacterial strains. At 14 days after the inoculation, the proximal colon, the longitudinal muscle-myenteric plexus (LMMP), and serum from vena cava, was collected from these animals and processed for further analysis.

Serum Serotonin Measurements by ELISA

Serum from blood samples collected from the vena cava was prepared using Microvette® 500 Z-Gel (Sarstedt) tubes after centrifugation (5 minutes; 10,000×g; room temperature (RT), 20-25° C.). Serotonin concentration in the serum samples was assessed using ELISA kit ADI-900-175 (Enzo Life Sciences), according to the manufacturer's instructions.

Tryptophan Metabolite Measurement in Broth by Mass Spectrometry (MS)—Broad MS Method Broth supernatant (50 μL) was extracted with 500 μL of methanol/acetic acid [99/1; v/v] containing d6-kynurenine 500 nM, d5-5-HIAA 1.25 μM and d4-Serotonin 250 nM as internal standards (Sigma-Aldrich, Stockholm, Sweden). After vortex and centrifugation, the samples were purified by transferring the supernatant through an OSTRO SPE 96-plate (Waters, Milford, MA) using a positive pressure manifold (Biotage AB, Uppsala, Sweden). After evaporation of the eluates under a stream of nitrogen at 40° C. the samples were reconstituted in 150 μL of injection solvent (methanol:water [10:90]+0.1% hydrochloric acid (v/v)). A standard curve containing serotonin, tryptophan, 5-HIAA, kynurenine, indole, tryptamine and 5-hydroxytryptophan (Sigma-Aldrich, Stockholm, Sweden) was made in methanol/acetic acid [99/1; v/v] and treated the same way as the samples. The samples and calibration curve sample were injected into a Waters Acquity UPLC system equipped with a Waters BEH C18 column (2.1×100 mm; 1.7 μm particle size). Column temperature was maintained at 60° C. and the flow rate was 0.4 mL/min. The temperature of the auto sampler was kept at 10° C. The mobile phases consisted of water with 0.1% formic acid (A) and acetonitrile with 0.1% formic acid (B). Gradient elution was performed starting off with isocratic elution with 1% B over 1 min. The gradient was then increased linearly from 1-15% B over 2 min followed by 15-99% B over 1 min. After 1 min of isocratic elution at 99% B the gradient returned to 1% B and held for 2 min for a total runtime of 7 min. Tryptophan metabolites was detected using a Xevo TQ-XS (Waters, Milford, MA) using positive electrospray. After optimization, the ion source parameters were: Capillary: 1.00 kV, desolvation temperature 500° C., desolvation gas flow 1000 L/h, cone gas flow 150 L/h, nebulizer gas pressure 7.0 bar, cone voltage (V) and collision energy (eV): serotonin 30 V and 10 eV; tryptophan 25 V and 25 eV; 5-HIAA 20 V and 20 eV; kynurenine 20 V and 18 eV; indole 50 V and 23 eV; tryptamine 20 V and 18 eV; 5-hydroxytryptophan 25 V and 18 Ev. The most intense precursor/product ion transition was selected. Consequently, the MRM transitions used were: serotonin m/z 177.1>160.3; tryptophan 205.2>118.25; 5-HIAA 192.4>146.2; kynurenine 209.1>146.1; indole 118.2>91.2; tryptamine 161.3>144.3; 5-hydroxytryptophan 221.2>162.2; d6-kynurenine 215.1>152.1; d4-serotonin 181.2>164.2; d5-5-HIAA 197.3>151.2. The dwell time was 24 ms.

Serotonin Measurement in Broth by Mass Spectrometry (MS)-Serotonin-Specific, Sensitive, MS Broth supernatant (50 μL) was extracted with 250 μL of methanol/acetic acid [99/1; v/v] containing serotonin (unlabeled) as a calibrator and d6-kynurenine 500 nm as an internal standard (Sigma-Aldrich, Stockholm, Sweden). After vortex and centrifugation, the samples were purified by transferring the supernatant through an OSTRO SPE 96-plate (Waters, Milford, MA) using a positive pressure manifold (Biotage AB, Uppsala, Sweden). After evaporation of the eluates under a stream of nitrogen at 40° C. the samples were reconstituted in 150 μL of injection solvent (methanol:water [10:90]+0.1% hydrochloric acid (v/v)). A standard curve containing serotonin (Sigma-Aldrich, Stockholm, Sweden) was made in methanol/acetic acid [99/1; v/v] and treated the same way as the samples. The samples and calibration curve sample were injected into a Waters Acquity UPLC system equipped with a Waters BEH C18 column (2.1×100 mm; 1.7 µm particle size). Column temperature was maintained at 60° C. and the flow rate was 0.4 mL/min. The temperature of the auto sampler was kept at 10° C. The mobile phases consisted of water with 0.1% formic acid (A) and acetonitrile with 0.1% formic acid (B). Gradient elution was performed starting off with isocratic elution with 1% B over 1 min. The gradient was then increased linearly from 1-15% B over 2 min followed by 15-99% B over 1 min. After 1 min of isocratic elution at 99% B the gradient returned to 1% B and held for 2 min for a total runtime of 7 min. Serotonin was detected using a Xevo TQ-XS (Waters, Milford, MA) using positive electrospray. After optimization, the ion source parameters were: Capillary: 1.00 kV, desolvation temperature 500° C., desolvation gas flow 1000 L/h, cone gas flow 150 L/h, nebulizer gas pressure 7.0 bar, cone voltage (V) and collision energy (eV): serotonin 30 V and 10 eV. The most intense precursor/product ion transition was selected. Consequently, the MRM transitions used were: serotonin m/z 177.1>160.3. The dwell time was 27 ms.

Results

Lactic acid producing bacterial strains are common inhabitants in the human gut and many lactic acid producing bacterial strains are also well-studied probiotic bacteria. The serotonin production capability of a number of *Lactobacillus* strains, including strains of the species *L. reuteri*, *L. plantarum*, *L. casei*, and *L. acidophilus*, was therefore tested with a broad mass spectrometry (MS) assay optimized for specific tryptophan metabolites, including serotonin, to identify bacterial strains with the ability to produce serotonin under anaerobic and aerobic conditions. With this method, all tested *L. reuteri* strains were found to produce serotonin when cultured anaerobically in DECT broth for 24 h (FIG. 1A and Table 1). Surprisingly, the *L. reuteri* bacterial strains were also found to produce serotonin when they were cultured aerobically in DECT broth for 24 h (FIG. 1A and Table 1). Importantly, and even more surprising, serotonin levels produced by the *L. reuteri* strains under aerobic conditions were markedly higher under aerobic conditions compared to under anaerobic conditions, resulting in a ratio of aerobic/anaerobic serotonin production of more than 1.0 (>1.0). Conversely, no serotonin production was found for the other tested bacterial strains, i.e., *L. casei* LMG 6904, *L. plantarum* 36E or *L. acidophilus* ATCC 4356, when they were cultured under anaerobic conditions (Table 1).

TABLE 1

Serotonin production in DECT, aerobic or anaerobic conditions (nM) for different *Lactobacillus* bacterial strains as measured by the broad MS method

| Bacterial strain | Serotonin production in DECT, aerobic conditions (nM) | Serotonin production in DECT, anaerobic conditions (nM) | Ratio aerobic/ anaerobic serotonin production |
|---|---|---|---|
| L. reuteri DSM 17938 | 7.0 | 1.8 | 3.9 |
| L. reuteri DSM 32846 | 10.0 | 2.5 | 4.0 |
| L. reuteri ATCC PTA 6475 | 6.1 | 1.7 | 3.6 |
| L. reuteri DSM 32848 | 8.8 | 1.0 | 8.8 |
| L. reuteri DSM 32849 | 7.8 | 1.0 | 7.8 |
| L. reuteri DSM 27131 | 9.1 | 3.1 | 2.9 |

TABLE 1-continued

Serotonin production in DECT, aerobic or anaerobic conditions (nM) for different *Lactobacillus* bacterial strains as measured by the broad MS method

| Bacterial strain | Serotonin production in DECT, aerobic conditions (nM) | Serotonin production in DECT, anaerobic conditions (nM) | Ratio aerobic/ anaerobic serotonin production |
|---|---|---|---|
| L. plantarum 36E | Not tested | 0.0 | n/a |
| L. casei LMG 6904 | Not tested | 0.0 | n/a |
| L. acidophilus ATCC 4356 | Not tested | 0.0 | n/a |

The three strains, *L. casei* LMG 6904, *L. plantarum* 36E and *L. acidophilus* ATCC 4356, were also tested for serotonin production using another, serotonin-specific and more sensitive, mass spectrometry method. Using this method, low, or very low, levels of serotonin were detected in the medium obtained from all these bacterial strains after culturing under anaerobic conditions (Table 2). No serotonin was, however, detected with this sensitive serotonin-specific method after culturing these bacterial strains under aerobic conditions (Table 2).

TABLE 2

Serotonin production in DECT, aerobic or anaerobic conditions (nM) for different *Lactobacillus* bacterial strains as measured by the serotonin-specific, sensitive MS method

| Bacterial strain | Serotonin production in DECT, aerobic conditions (nM) | Serotonin production in DECT, anaerobic conditions (nM) |
|---|---|---|
| L. plantarum 36E | 0.0 | 0.3 |
| L. casei LMG 6904 | 0.0 | 0.1 |
| L. acidophilus ATCC 4356 | 0.0 | 0.9 |

These results indicate that some, but not all, lactic acid producing bacterial strains are capable of producing serotonin under anaerobic and/or aerobic conditions. Also, some lactic acid producing bacterial strains are capable of producing serotonin under anaerobic conditions, but incapable of producing serotonin under aerobic conditions. The results also demonstrate that different lactic acid producing bacterial strains are better serotonin producers than other lactic acid producing bacterial strains under in vitro conditions mimicking in vivo conditions of the gastrointestinal tract.

Figure 1B:
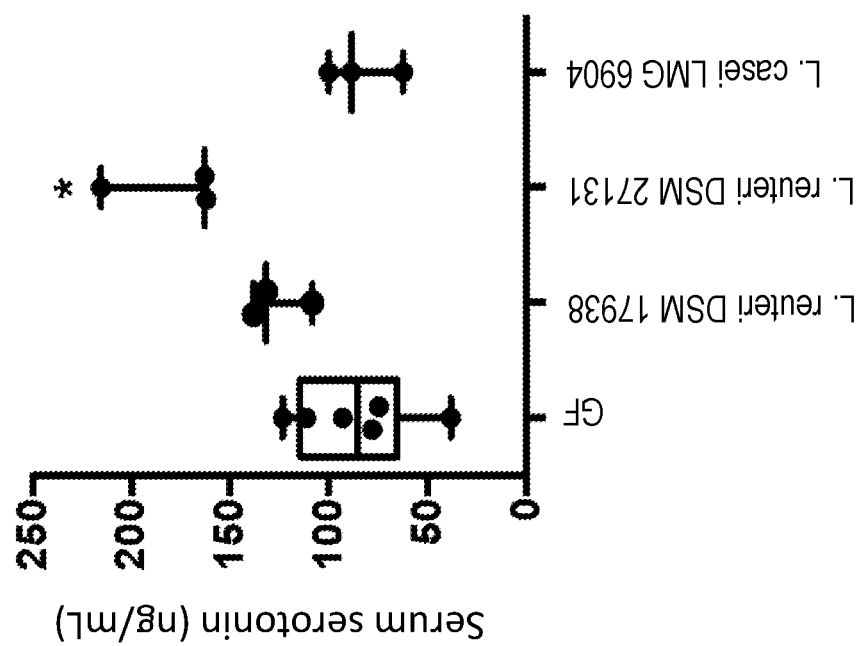

In further experiments, and to investigate if serotonin produced by *L. reuteri* bacterial strains was bioactive and could be transported into, and contribute to, the circulating serotonin pool in vivo in Tph1-/- GF mice. These mice, which are deficient in endogenous serotonin production, were inoculated with *L. reuteri* DSM 17938 or *L. reuteri* DSM 27131. An increase in the Tph1-/- GF mouse serum serotonin levels was observed using ELISA after inoculation with either of the *L. reuteri* strains (FIG. 1B), and the increase was more pronounced with DSM 27131 as compared to with DSM 17938. In contrast, when GF Tph1-/- mice were inoculated with *L. casei* LMG 6904, which did not produce serotonin in vitro (FIG. 1A, Table 1, Table 2), serum levels of serotonin did not increase (FIG. 1B). The results of these experiments clearly show that specific *Lactobacillus* species, and specific lactic acid producing bacterial strains, have the ability to produce serotonin locally in the gastrointestinal tract, which is bioavailable to the host and can be transported from the gastrointestinal tract to the periphery, thus, contributing both to the gastrointestinal, and to the systemic, serotonin pool.

The results therefore indicate that *L. reuteri* DSM 17938 and *L. reuteri* DSM 27131 are examples of lactic acid producing bacterial strains that could be selected based on their aerobic serotonin production, high ratio of aerobic/anaerobic serotonin production and that they could be used to increase serotonin levels in vivo. These two bacterial strains, and other lactic acid producing bacterial strains, such as the *L. reuteri* bacterial strains of Table 1, with the same or similar ability to produce serotonin under aerobic conditions, can thus be considered effective in treating serotonin deficiency and diseases related to serotonin deficiency. On the other hand, although capable of producing low levels of serotonin under anaerobic conditions, a bacterial strain such as *L. plantarum* 36E, *L. casei* LMG 6904, or *L. acidophilus* ATCC 4356, would not be selected or considered effective in treating serotonin deficiency based on their incapability of producing serotonin under aerobic conditions in vitro.

Example 2—In Vitro and In Vivo Production of Serotonin and Assessment of Additional Suitable Bacterial Strains Since the *Lactobacillus reuteri* bacterial strains in Example 1 were found to be good producers of serotonin under both anaerobic and aerobic conditions, a number of additional *L. reuteri* bacterial strains (Table 3) were assessed for their serotonin production.

Materials and Methods

All bacterial culturing and serotonin measurement methods were performed as described in Example 1 using the serotonin-specific and sensitive MS method. The lactic acid producing bacterial strains tested in this Example and the detected levels of serotonin are listed in Table 3 below.

Results

The additional *L. reuteri* bacterial strains were cultured both anaerobically and aerobically in DECT for 24 h and the concentration of serotonin in the respective culture medium was then assessed (Table 3). It was found that all these additional *L. reuteri* bacterial strains were capable of producing low, but detectable, amounts of serotonin under anaerobic conditions. It was further found that all these *L. reuteri* bacterial strains produced more serotonin under aerobic conditions compared to under anaerobic conditions (Table 3). All these *L. reuteri* strains were, could thus be selected as suitable strains according to the invention for use in the treatment of serotonin deficiency and diseases related to serotonin-deficiency.

TABLE 3

Serotonin production in DECT, aerobic or anaerobic conditions (nM) for additional *Lactobacillus reuteri* bacterial strains, as measured with the serotonin-specific sensitive MS method

| Bacterial strain | Serotonin production in DECT, aerobic conditions (nM) | Serotonin production in DECT, anaerobic conditions (nM) | Ratio aerobic/anaerobic serotonin production |
|---|---|---|---|
| *L. reuteri* DSM 27131 | 1.1 | 0.4 | 2.8 |
| *L. reuteri* DSM 32465 | 1.3 | 0.4 | 3.3 |
| *L. reuteri* ATCC PTA 6475 | 0.8 | 0.7 | 1.1 |
| *L. reuteri* DSM 33634 | 0.8 | 0.4 | 2.0 |
| *L. reuteri* DSM 33635 | 1.3 | 0.4 | 3.3 |
| *L. reuteri* ATCC PTA 5289 | 1.3 | 0.5 | 2.6 |
| *L. reuteri* DSM 33632 | 1.5 | 0.4 | 3.8 |
| *L. reuteri* DSM 33633 | 1.4 | 0.2 | 7.0 |
| *L. reuteri* DSM 33509 | 0.9 | 0.2 | 4.5 |

Example 3—Bacterially Produced Serotonin has Effects In Vivo on ENS Development and is Critical for Crypt Innervation in the Colon Material and Methods Bacterial Culture, Mouse Caecum The caecum was collected from conventional Tph1+/+ mice and cultured in DECT under anaerobic conditions at 37° C. for 48 h. At this time point, samples were centrifuged (10,000×g, 4° C., 2 min) and the pellet was collected. Pellets were preserved in 20% glycerol (cryoprotectant) and frozen at −80° C. until use.

Bacterial Culture, *Lactobacillus*

For in vivo experiments, *L. reuteri* DSM 27131 and the *L. casei* LMG 6904 were cultured in MRS under anaerobic conditions. Each culture was sampled at 24 h and the samples were centrifuged (10,000×g, 4° C., 2 min). The pellets were preserved in 20% glycerol (cryoprotectant) and frozen at −80° C. until use.

Mouse Inoculation Experiments, Mouse Caecum and *Lactobacillus*

For these experiments, mouse caecum, 48 h cultures of mouse caecal content in DECT broth or 24 h cultures of *L. reuteri* DSM 27131 and *L. casei* LMG 6904 in MRS were used. The pellets obtained from the mouse caecum and the *Lactobacillus* cultures were resuspended in a hungate tube containing 5 mL sterile reducing buffer (reduced and sterile PBS mixed with $Na_2S.9H_2O$ 0.24 g/L and cysteine 0.5 g/L in the presence of $NaHCO_3$ 4 g/L). Adult Tph1−/− mice were transferred to an experimental isolator and fasted for 4 h. The mice were gavaged with 200 μL of either solution containing the bacteria from mouse caecum or *Lactobacillus*. At 14 days after the inoculation, the proximal colon, the LMMP, the sera from vena cava, the luminal content of the colon and the caecum were collected from these animals.

Immunohistochemistry

Proximal colon samples were fixed in PFA 4% at 4° C. overnight and kept in 70% EtOH at 4° C. before sectioning. Tissue was embedded in paraffin and 10 μm-thick sections deparaffinized by sequential steps (TissuClear 2×12 minutes; 99% EtOH 2×2 minutes; 95% EtOH 2×2 minutes) with Leica System. For antigen retrieval, the slides were incubated with 10 mM sodium citrate/0.05% TWEEN® 20 solution (pH 6.0), warmed in water bath (95° C.) during 20 min, incubated at RT during 20 min and rinsed twice with PBS-0.05% TWEEN® 20. Next, the slides were incubated with a blocking solution (PBS/4% BSA/4% donkey serum) during 1 h, at RT; the primary antibody (Table 4) diluted in the blocking solution overnight, at 4° C.; the secondary antibody (Table 4) diluted in the blocking solution during 1 h at RT; and Hoechst solution during 5 min at RT. From the incubation with primary antibody, each incubation step was followed by two wash steps in PBS. The slides were mounted with mounting medium (Dako).

TABLE 4

Antibodies for immunohistochemistry

|  | Manufacturer | Reference | Dilution |
|---|---|---|---|
| Primary antibodies | | | |
| Rat anti-serotonin | Abcam | ab6336 | 1/400 |
| Rabbit anti-PGP9.5 | Sigma-Aldrich | SAB4503057 | 1/400 |
| Rabbit anti-TUJ1 | Abcam | ab18207 | 1/400 |
| Secondary antibodies | | | |
| Donkey anti-rat 488 | Life technologies | A21208 | 1/500 |
| Donkey anti-rabbit 568 | Life technologies | A10042 | 1/500 |

After dissection, the LMMP samples were fixed in PFA 4% at 4° C. overnight and rinsed with cold PBS 3 times for 10 min. Next, the LMMPs were kept in NaN$_3$ solution (NaN$_3$ 0.1% diluted in PBS) at 4° C. until immunostaining. The LMMP samples were incubated in 300 µl blocking solution (Triton X100 0.5%, BSA 4% and donkey serum 4% in NaN$_3$ 0.1% solution) for 1 h. Next, the tissues were incubated overnight with the primary antibody (Table 4) diluted in blocking solution followed by washes with PBS 3 times, 10 min and incubated with the secondary antibody (Table 4) for 1.5 h. The tissues were washed with PBS 3 times, 10 min and incubated with Hoechst solution for 5 minutes and washed again with PBS 3 times, 10 min. LMMP samples were mounted with fluorescent mounting solution medium. The immunostained tissue was imaged by confocal microscopy using a Zeiss Laser Scanning Inverted Microscope LSM-700 equipped with 20×/0.8 NA objectives and Black Zen software (Carl Zeiss).

PGP9.5 and TuJ1 are well-established markers for mature enteric neurons. For the proximal colon, the percentage of the immunopositive area for PGP9.5 or TUJ1 inside the colonic tissue was therefore quantified and the number of epithelial cells positive for serotonin were counted and divided by the mucosa area. 2-3 images were analyzed per tissue and 3 tissue samples per animal were analyzed.

For the ENS immunostaining, the fluorescent area positive for serotonin was quantified. 2-3 images per tissue sample were analyzed.

Results

Figure 2C:
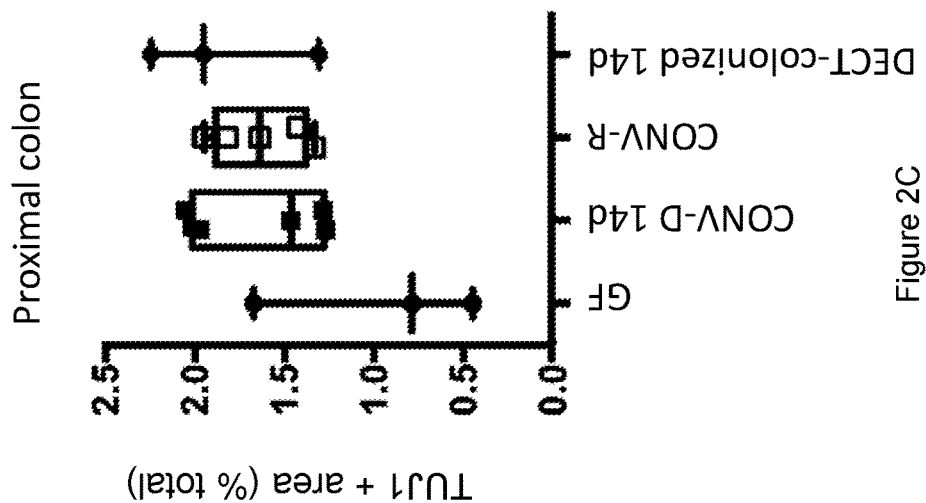
FIG. 2. Bacterially produced serotonin has local effects within the gastrointestinal tract and is critical for enteric nervous system (ENS) maturation and crypt innervation within the proximal colon. The graphs illustrate the serotonin-positive area in colonic longitudinal muscular myenteric plexus (LMMP) (A, D); the PGP9.5-positive area of the colonic crypt (B, E); and the TUJ1-positive area in the colonic crypt (C, F). (A-C) GF in the graphs indicates Tph1−/− germ free animals; CONV-D 3d and CONV-D 14d indicates Tph1−/− germ free animals inoculated with Tph1+/+ mouse caecum for 3 or 14 days, respectively; CONV-R indicates Tph1−/− animals with a normal microbiota; and DECT-colonized 14 d indicates Tph1−/− germ free animals inoculated with mouse caecal content, which had been cultured for 48 h in DECT prior to inoculation (n=3-6/group). Results in D-F represent data obtained from GF Tph1−/− mice, at 14 days after inoculation with *L. reuteri* DSM 27131 or *L. casei* LMG 6904 (n=3-6/group). (A) The data shows that inoculation with mouse caecal microbiota increases the levels of serotonin in the enteric neurons of the proximal colon compared to the levels of serotonin in the ENS of GF Tph1−/− mice. The serotonin levels in the ENS after 3 days is restored almost to the same levels as in the CONV-R mice. (B, C) The data also shows that presence of the mouse caecal microbiota in the gastrointestinal tract increases well-established markers of mature enteric neurons (PGP9.5 and Tuj1). The data in D shows that serotonin levels are also increased in the enteric neurons of the proximal colon after inoculation with a single probiotic bacterial strain, *L. reuteri* DSM 27131, whereas *L. casei* LMG 6904 has no effect on enteric neuron serotonin levels. In addition, inoculation with *L. reuteri* DSM 27131 increased the maturity of enteric neurons, as visualized with the markers PGP9.5 and Tuj1 (E, F), whereas *L. casei* LMG 6904 had no effect on these two markers for enteric neuron maturity. Data are presented as box plots showing maximum, minimum, median, and interquartile range. Each dot represents a single mouse. The normality of each group was analyzed before the statistical significance was evaluated by Student's t test (if data was normally distributed) or Mann- Whitney test. If more than two groups were compared data was analyzed using one-way Anova followed by post hoc Tukey's multiple comparisons tests if data was normally distributed, otherwise Kruskal-Wallis test followed by post hoc Dunn's multiple comparisons were performed. The level of significance was set at *$p<0.05$; **$p<0.01$.
Figure 2B:
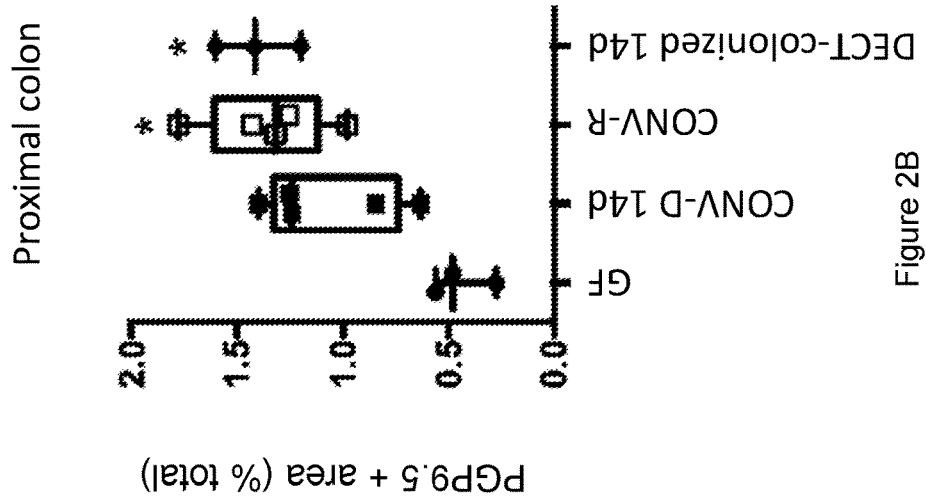
Figure 2A:
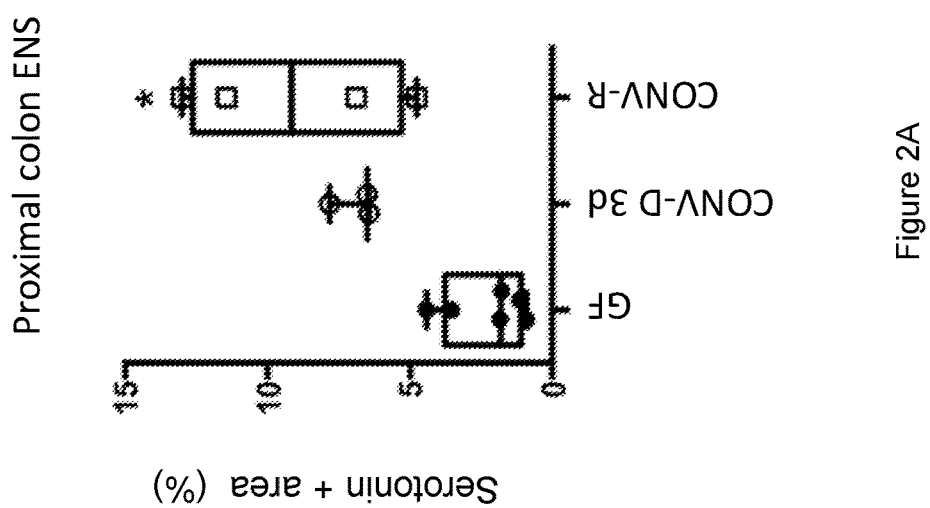
Figure 2F:
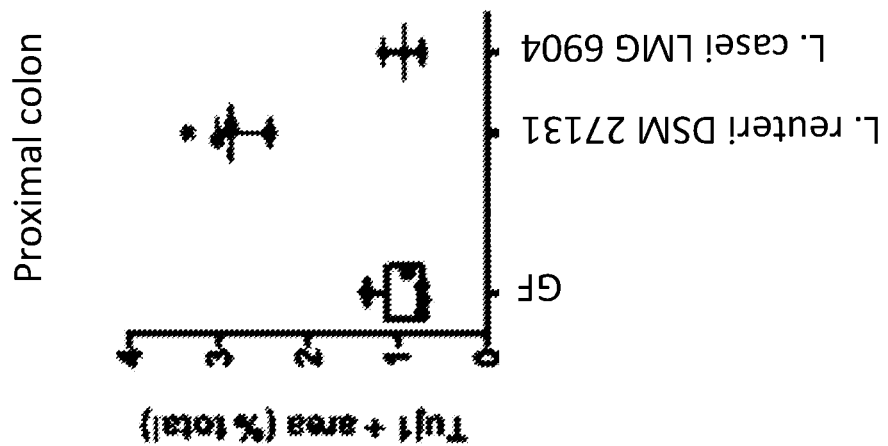
Figure 2E:
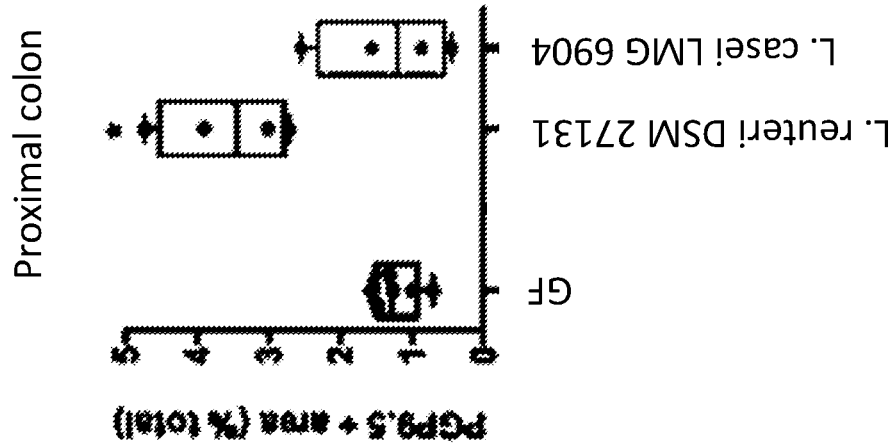
Figure 2D:
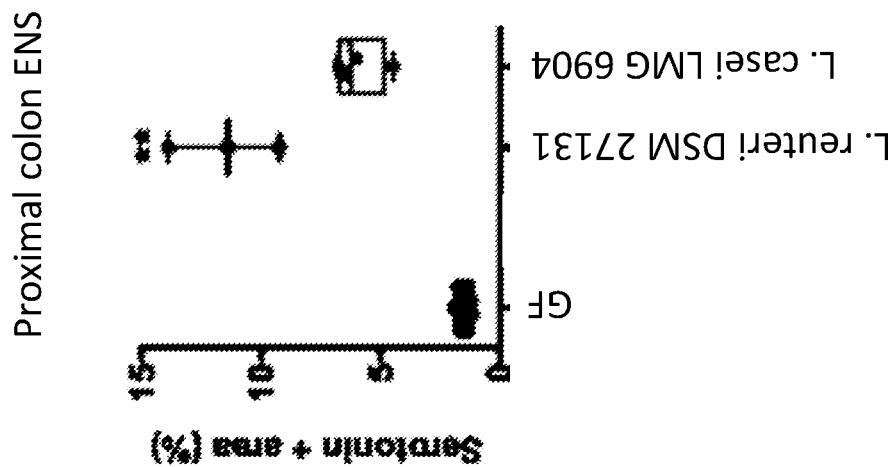

Since serotonin is essential for the normal development and maturation of the ENS, the effect of microbially produced serotonin on mouse ENS development was investigated (FIGS. 2A-2F). Immunostaining revealed that colonization of GF Tph1–/– mice with mouse caecal microbiota increased serotonin levels within enteric neurons of the proximal colon (FIG. 2A). Presence of a caecal microbiota also increased well-established markers of mature enteric neurons, PGP9.5 and TUJ1, within the colonic tissue (FIGS. 2B and 2C) demonstrating that bacterially produced serotonin plays a role in the ENS development and maturation. GF Tph1–/– mice were also inoculated with *L. reuteri* DSM 27131 or *L. casei* LMG 6904 for 14 days and assessed for ENS replenishment with serotonin. It was found that inoculation with *L. reuteri* DSM 27131, which had previously been shown to produce serotonin under aerobic conditions in vitro as well as in vivo, increased the neuronal serotonin level (FIG. 2D) and DSM 27131 also increased markers of mature neurons, PGP9.5 and Tuj1, in the proximal colon, while the non-serotonin-producing *L. casei* LMG 6904 did not affect either neuronal serotonin levels or markers of neuronal maturity in the proximal colon.

Example 4—Isolation and Selection of Serotonin Producing Human Bacterial Strains Material and Methods Human Feces Collection The human feces samplings were done from three healthy donors between 30-50 years old. The volunteers where treatment-naïve and had not taken any antibiotics. The human fecal sampling and the following use of the samples were performed in accordance with the ethical policies and regulations of Sweden.

Bacterial Culture—Human Feces

Freshly voided human feces (1% (w/v) inoculum) was inoculated in DECT broth, either under anaerobic condition, i.e., in a Coy chamber, or under ambient aerobic conditions. Each culture was sampled at different time points (0 h, i.e., before inoculation, 12 h, 24 h, 36 h, 48 h, 60 h) and the samples were centrifuged (10,000×g, 4° C., 2 min). The supernatants and pellets were frozen at −80° C. Supernatants were used for serotonin measurements and pellets were used to analyze the bacterial community within the samples by utilizing 16S rRNA gene analysis. One glycerol-stock of each sample was also kept from each time-point as described above.

Isolation of Bacterial Serotonin Producers

DECT broth was made according to Example 1. LYBHI media contained Brain Hearth Infusion (BHI) 3.7% (Oxoid Fisher-Scientific #CM1135), L-cysteine 0.05% (Sigma-Aldrich #W326305), D-(+)-cellobiose 0.1% (Sigma-Aldrich #22150), maltose 0.1%, and hemin 0.0006% (Sigma-Aldrich #51280). To obtain anoxic varieties of DECT and LYBHI, cysteine 0.05%, was added as reducing agent. The growth medium was autoclaved for 30 min, 15 PSI at 121° C. 36 h glycerol stocks obtained from human feces cultured in DECT broth was plated in LYBHI (LYBHI broth with 2% agar; Nordic Biolabs #214010), DECT (DECT broth with 2% agar) and MRS (50 g of MRS powder from Sigma-Aldrich (Sigma-Aldrich #69966) and 1 ml of TWEEN® 80 (Sigma-Aldrich #P8074) in 1 L of distilled water with 2% agar) plate under anaerobic conditions. The plating was performed 3 times meaning a second culture plate was done from a sampling of the most enriched area in the first plate onto a second plate, and from the second plate to a third plate. Each isolated colony was then cultured in LYBHI, DECT and MRS, respectively to make glycerol stocks and to harvest the DNA after centrifugation (10,000×g, 4° C., 2 min). DNA harvesting was done in order to perform 16S rRNA gene sequencing to identify each bacterial strain. The purity of each isolate was checked by Gram staining. For serotonin production kinetics, each isolate was cultured in DECT broth, for 24 h, under aerobic and anaerobic conditions. Thereafter, samples from the cultures were collected and centrifuged (10,000×g, 4° C., 2 min) to harvest the supernatant and analyze the levels of serotonin.

Extraction of Total Fecal Genomic DNA Genomic

DNA was isolated from the pellet obtained from 1.5 ml of culture sample using the NucleoSpin Soil kit (MACHEREY-NAGEL, Germany) according to the manufacturer's instruction but with a modification of the cell lysis step. Samples were suspended in SL2 buffer added with SX and then mixed in a vortex with a horizontal adaptor at maximum speed for 2 minutes. Cells were lysed by heating at 90° C.

for 10 minutes followed by bead beating three times at 5.5 m/s for 60 s using the FastPrep-24 Instrument (MP Biomedicals). The heating and bead beating steps were repeated one additional time and the supernatants from the two extractions were pooled prior to purification using the columns in the kit. DNA was eluted using elution buffer and DNA concentration and quality was checked using a NanoDrop spectrophotometer.

16S rRNA Gene Sequencing and Identification of the Isolates

The full length of 16S rRNA gene was amplified using 27F and 1492R primers designed for dual indexing (Appl Environ Microbiol 79: 5112-5120 (2013)). Each sample was amplified in 50 µL reactions containing HotStarTaq Master Mix 2× (QIAGEN), 10 µmol/L of each primer and 250 ng of genomic DNA. PCR was carried out under the following conditions: initial denaturation for 5 min at 94° C., followed by 26 cycles of denaturation for 30 s at 94° C., annealing for 40 s at 52° C. and elongation for 90 s at 72° C., and a final elongation step for 7 min at 72° C. Samples were purified with the NucleoSpin Gel and PCR Clean-up kit (MachereyNagel) and quantified using a NanoDrop spectrophotometer. Dilutions of 10 ng/µl in a volume of 40 µL were prepared and sent send for sequencing to Eurofins. The forward and the reverse amplified sequences were obtained for each isolate and aligned to find the consensus sequence. The consensus sequence was then blasted using Basic Local Alignment Search Tool from NCBI to identify the bacteria.

Serotonin Measurement in Broth by the Serotonin-Specific Sensitive MS Method

Serotonin produced by these bacterial strains was quantified using the serotonin-specific and sensitive mass spectrometry method as described in Example 1.

Results

Serotonin Production

Figure 3:
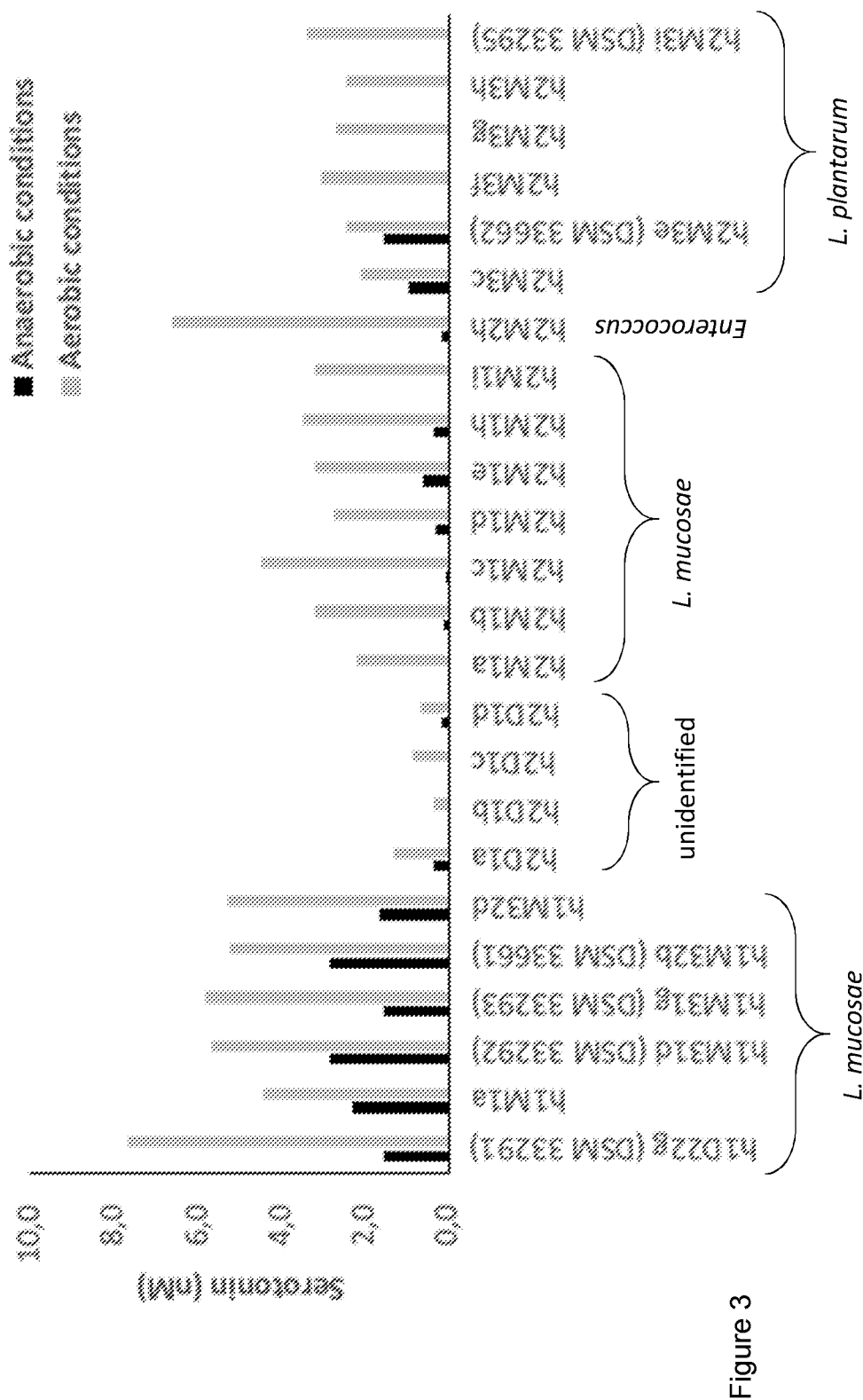
FIG. 3. Serotonin production by bacterial strains isolated from human donors. Of a total of 199 isolates obtained from two human donors, 24 isolates, as shown in the graph, were found to produce serotonin under anaerobic and/or aerobic conditions in vitro. A total of six isolates from donor #1 and one isolate from donor #2 were found to produce more than 1 nM of serotonin in DECT broth under anaerobic conditions in vitro, whereas all six isolates from donor #1, and 15 isolates from donor #2 produced more than 1 nM serotonin under aerobic conditions. Interestingly, the majority of these strains were found to produce almost twice as much serotonin under aerobic conditions as compared to under anaerobic conditions. Sequencing analysis identified the serotonin producing isolates as strains of *L. mucosae* (n=13), *L. plantarum* (n=6), and *Enterococcus* (n=1). Four isolates could not be identified, but these isolates were closely aligned with *Escherichia*, *Shigella*, or *Brenneria* bacterial strains.

To identify serotonin producing microbes from the human gut, fecal samples from the two donors with the highest total serotonin production, i.e., donor #1 and donor #2, were cultured in DECT under anaerobic conditions. In total, 199 isolates were obtained; 122 bacterial isolates from donor #1 and 77 from donor #2 using LYBHI, DECT and MRS agar plates. The levels of serotonin production by these isolates were then determined by growing the obtained isolates as single cultures under either anaerobic or aerobic conditions. Of the 199 isolates, only six isolates from donor #1 and 11 isolates from donor #2 produced detectable levels of serotonin in DECT broth under anaerobic conditions (Table 5; FIG. 3). Of the 199 isolates, 24 isolates in total were found to produce serotonin under aerobic conditions and these isolates included those isolates that also produced serotonin under anaerobic conditions. For all these 24 isolates, serotonin production was improved under aerobic conditions compared to under anaerobic conditions. The full-length 16S rRNA sequencing analysis identified the 24 isolates as *Lactobacillus mucosae* (n=13), *Lactobacillus plantarum* (n=6), and *Enterococcus* spp. (n=1) (Table 5). Finally, four isolates from donor #2 were not clearly identified, but these isolates were closely aligned with *Escherichia*, *Shigella*, or *Brenneria* bacterial strains (Table 5). Nonetheless, these results suggest an important role of the genus *Lactobacillus*, and especially an important role for *Lactobacillus mucosae* and *Lactobacillus plantarum* bacterial strains, in serotonin production, both under anaerobic and aerobic conditions.

Good serotonin producing lactic acid producing bacterial strains under aerobic conditions belonging to either *L. mucosae* or *L. plantarum* were selected (Table 5). In more detail, bacterial strain *L. mucosae* h1D22g, h1M31d, h1M31g, and h1M32d, and *L. plantarum* h2M3E and h2M3i were selected and deposited at DSMZ (corresponding deposit numbers DSM 33291, DSM 33292, DSM 33293, DSM 33661, DSM 33662, and DSM 33295, respectively) based on their serotonin production under aerobic conditions.

TABLE 5

Isolated human serotonin producing strains and serotonin production in vitro as measured with the serotonin-specific sensitive MS method

| ID | 16S rRNA identification | Serotonin production in DECT, aerobic conditions (nM) | Serotonin production in DECT, anaerobic conditions (nM) | Ratio serotonin production aerobic/anaerobic conditions |
|---|---|---|---|---|
| h1D22g; DSM 33291 | *Lactobacillus mucosae* | 7.7 | 1.5 | 5.1 |
| h1M1a | *L. mucosae* | 4.5 | 2.3 | 2.0 |
| h1M31D; DSM 33292 | *L. mucosae* | 5.7 | 2.9 | 2.0 |
| h1M31g; DSM 33293 | *L. mucosae* | 5.8 | 1.6 | 3.6 |
| h1M32b; DSM 33661 | *L. mucosae* | 5.2 | 2.8 | 1.9 |
| h1M32d | *L. mucosae* | 5.3 | 1.7 | 3.1 |
| h2D1a | unknown | 1.3 | 0.4 | 3.25 |
| h2D1b | unknown | 0.4 | 0.03 | 13.3 |
| h2D1c | *Escherichia fergusoni coli*; *Shigella sonnei, boydii, flexneri*; *Brenneria alni\** | 0.9 | 0.0 | n/a |
| h2D1d | *E. fergusoni coli*; *S. sonnei, flexneri*; *B. alni\** | 0.7 | 0.2 | 3.5 |
| h2M1a | *L. mucosae* | 2.2 | 0.0 | n/a |
| h2M1b | *L. mucosae* | 3.2 | 0.1 | 32.0 |
| h2M1c | *L. mucosae* | 4.5 | 0.1 | 45.0 |
| h2M1d | *L. mucosae* | 2.8 | 0.3 | 9.3 |
| h2M1e | *L. mucosae* | 3.2 | 0.6 | 5.3 |
| h2M1h | *L. mucosae* | 3.5 | 0.4 | 8.8 |
| h2M1i | *L. mucosae* | 3.2 | 0.000 | n/a |
| h2M2h | *Enterococcus faecium, hirae, durans, mundti\** | 6.6 | 0.2 | 33.0 |
| h2M3c | *L. plantarum* | 2.1 | 1.0 | 2.1 |
| h2M3e; DSM 33662 | *L. plantarum* | 2.5 | 1.5 | 1.7 |
| h2M3f | *L. plantarum* | 3.1 | 0.0 | n/a |
| h2M3g | *L. plantarum* | 2.7 | 0.0 | n/a |
| h2M3h | *L. plantarum* | 2.4 | 0.0 | n/a |
| h1M3i; DSM 33295 | *L. plantarum* | 3.4 | 0.0 | n/a |

*It was not possible to identify the species of this isolate and the 16S rRNA based identification gave all listed species as potential species of the isolate.

Example 5—Mouse Inoculation Experiments with Human Serotonin Producing Bacterial Strains Materials and Methods Mouse Inoculation with Human Serotonin Producing Bacterial Strains Mouse inoculations were performed using germ free Tph1-/- mice. The animals were inoculated with either *Lactobacillus mucosae* DSM 33661 or *Lactobacillus plantarum* DSM 33662 using the same method as described in Example 3. Serum and gut lumen samples, as well as tissue from the proximal colon, were collected at 14 days after inoculation and analyzed for serotonin.

Serotonin Measurements in Serum and Gut Lumen by ELISA

Serum from blood samples collected from vena cava was prepared using Microvette® 500 Z-Gel (Sarstedt) tubes after centrifugation (5 minutes; 10,000×g; room temperature (RT), 20-25° C.). Luminal content of the gastrointestinal tract was sampled from the proximal colon or from caecum. Luminal contents were weighed and snap frozen. Serotonin from the luminal contents was then extracted as following. A volume of Tris-HCl 25 mM/EDTA 1 mM/EGTA 1 mM solution was added to each sample (w/v as 1 mg/2 µL), homogenized with 5 mm steel beads and TissueLyser (Qiagen, 25 Hz, 2 min), incubated overnight at 4° C. and centrifuged at 4° C., 20 min, 10,000×g. The supernatant of each sample was collected and kept at −80° C. until analysis. Broth supernatants were obtained from bacterial cultures to measure serotonin and uncultured broth was used as blank. Serotonin from all samples was assessed using ELISA kit ADI-900-175 (Enzo Life Sciences), according to the manufacturer's instructions.

Serotonin Immunopositive Area in the Proximal Colon

The serotonin immunopositive in tissue samples from the proximal colon area was analyzed and quantified as described in Example 3.

Results

Figure 4C:
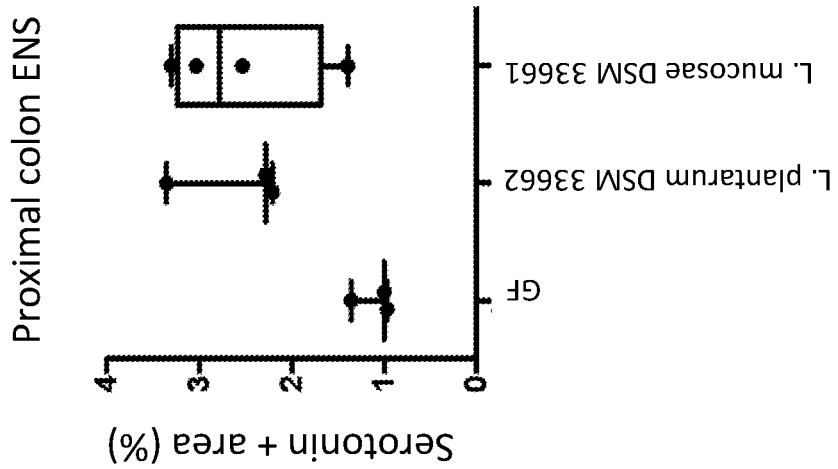
FIG. 4. Selected isolated human bacterial strains produce functional serotonin in vivo. Two of the bacterial strains isolated from human donors, which were found to produce serotonin in vitro under both anaerobic and aerobic conditions, *L. plantarum* DSM 33662 and *L. mucosae* DSM 33661, were selected and used to inoculate germ free Tph1–/– mice. The graph shows that these bacterial strains increased serotonin levels in vivo, both locally within the gut lumen (A) and also in the systemic circulation (serum samples) (B) as compared to the levels found in the germ free Tph1–/– mice. In addition, both strains increased the serotonin positive area in the ENS of the proximal colon (C). These bacterial strains are therefore capable of increasing serotonin levels locally in the in the gut lumen (caecum) in vivo and this locally produced serotonin is bioactive and can be transported into the systemic circulation (serum) and into neurons of the enteric nervous system of the proximal colon. Data are presented as box plots showing maximum, minimum, median, and interquartile range. Each dot represents a single mouse.
Figure 4B:
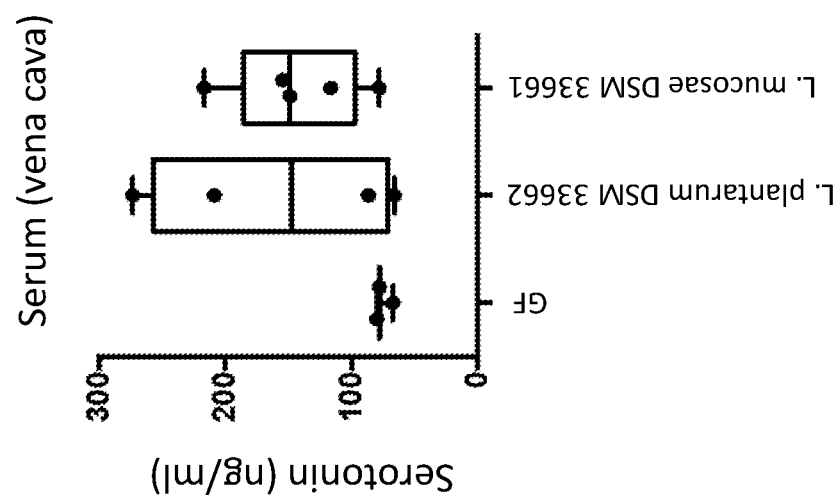
Figure 4A:
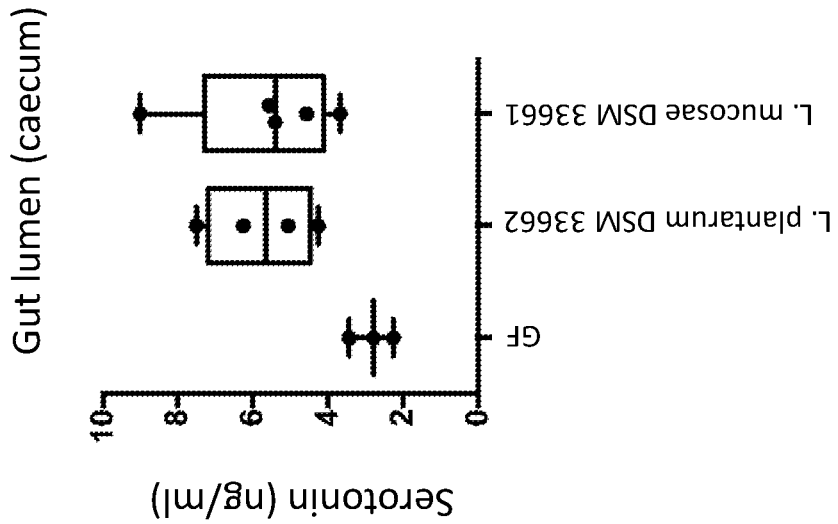

The two isolated human bacterial strains, *L. mucosae* DSM 33661 and *L. plantarum* DSM 33662, were selected based on their serotonin production under anaerobic and aerobic conditions in vitro. These strains were found to produce functional serotonin also in vivo (FIG. 4). The graph shows that both these bacterial strains were capable of increasing serotonin levels both locally in the gut lumen (FIG. 4A) and in the systemic circulation (serum samples, FIG. 4B) as compared to the levels found in the corresponding germ-free mice. In addition, both these human strains were found to increase the serotonin positive area in the ENS of the proximal colon (FIG. 4C). These human bacterial strains are therefore capable of increasing serotonin levels locally in the in the gut lumen (caecum) in vivo and this locally produced serotonin is bioactive and can be transported into the systemic circulation (serum) and into neurons of the enteric nervous system of the proximal colon. The results indicate that human commensal bacterial strains producing serotonin can be isolated, identified and selected to increase serotonin levels in vivo.

Example 6—Adhesion to Mucus by Serotonin Producing Bacterial Strains

Materials and Methods

Preparation of Mucus and Plate Coating

Mucus was prepared from pig small intestine. The inside of 5 cm intestine was scraped with a spatula and material removed and collected in 5 ml ice-cold PBS. The resulting suspension was centrifuged first at 11,000×g for 10 min and then at 26,000×g for 15 min in order to remove cells and particulate matter. The mucus preparation was stored at −20° C. until use. The mucus material was diluted to A280=0.1 (absorbance at 280 nm=0.1) in PBS pH 6.0 and incubated overnight in microtiter wells (Nunc MaxiSorb) (150 µl per well) at 4° C. with slow agitation. The wells were thereafter washed with PBS (pH 6.0) with 0.05% TWEEN® 20 (PBST), thereafter blocked with 0.2 ml PBS pH 6.0 with 1% TWEEN® 20 for 1 h and finally washed twice with PBST.

Preparation of Bacteria

Mucus adhesion experiments were performed with the following bacterial strains: *Lactobacillus reuteri* DSM 27131, DSM 32465, DSM 33632, DSM 33633, DSM 33634, DSM 33635, and DSM 33509; *Lactobacillus mucosae* DSM 33291, DSM 33292, DSM 33293, and DSM 33661; and *Lactobacillus plantarum* DSM 33662. Each *Lactobacillus* strain was inoculated from a frozen stock at −70° C. and grown in 10 ml MRS broth (Merck) for 16 h at 37° C. OD was measured at 600 nm and the sample was diluted to OD 0.5 (total volume being 1 ml). The diluted bacterial solutions were thereafter washed twice with PBST pH 7.4 and re-suspended in PBST pH 6.0. After final washing and re-suspension in PBST pH 6.0, the bacteria were diluted and plated on MRS agar for analyzing the start value (colony forming units (cfu)/ml) The same bacterial suspensions were used for the binding experiment.

Mucus Binding, Trypsin Release and Quantification

Bacterial suspensions (150 µl) were added to each well and incubated for 4 h at 37° C. with slow agitation. The wells were washed 4 times with PBST, pH 6.0, to remove unbound bacteria. After washing, 150 µL trypsin EDTA solution (0.25% porcine trypsin and 1 mM EDTA.4Na in Hanks' Balanced Salt Solution) was added to the wells and incubated at 37° C. for 30 min. Then, the released bacteria were mixed thoroughly, serially diluted and plated on MRS agar plates. The plates were incubated at anaerobic conditions for 24 h at 37° C. whereafter the colonies were counted (colony forming units (cfu)) and the number of adhering bacteria per well calculated.

Results

It was investigated whether serotonin producing lactic acid bacteria are also capable of attaching to mucus in vitro, which would indicate that they could do so also in vivo, in particular to the intestinal mucosa, and thereby enable uptake of bacterially produced and secreted serotonin by the intestinal mucosa, and in particular by the intestinal epithelium. The bacterial strains tested for adhesion were selected based on their ability to produce serotonin under aerobic conditions. It was found that *L. reuteri* DSM 27131, which is capable of producing serotonin under aerobic conditions in vitro and which is also able to contribute to the systemic pool of serotonin in vivo, is capable of attaching to mucus (FIG. 10A). This ability was also observed and further increased with all other tested *L. reuteri* strains (DSM, 32465, DSM 33632, DSM 33633, DSM 33634, DSM 33635, and DSM 33509), and also with all other tested *L. mucosae* strains (DSM 33291, DSM 33292, DSM 33293, DSM 33661) and *L. plantarum* strain DSM 33662) (FIGS. 10A and 10B). The adhesion ability of each of the *L. reuteri* bacterial strains DSM 33632, DSM 33633, DSM 33634, DSM 33635, and DSM 33509 was also found to be improved as compared to the adhesion ability of their corresponding parent strain (data not shown). These results indicate that certain lactic acid bacterial strains of the species *Lactobacillus reuteri*, *Lactobacillus mucosae*, and *Lactobacillus plantarum* are able to attach to the intestinal mucosa, where metabolites, such as serotonin, can then be produced and secreted close to the intestinal epithelium lining the gastrointestinal tract.

Example 7—Manufacture of an Oil-Based Formulated Probiotic Product for Use in Serotonin Deficiency In this example, a probiotic product for use in serotonin deficiency is manufactured. A lactic acid producing bacterial strain capable of producing serotonin under aerobic conditions is selected as disclosed herein, such any of the *Lactobacillus* bacterial strains in Examples 1, 2, 4 or 6. These strains are then grown separately as pure cultures and lyophilized, using standard methods for growing *Lactobacillus* bacterial strains in the industry. The product is an oil-based formulation with a single (pure) bacterial strain made for good stability and shelf life. The unique feature of the production process is a step of drying the oil by placing it under vacuum to remove most of the water in the oil and to increase the stability of the formulation. The oil used herein is a pure edible vegetable oil, preferably sunflower oil and medium-chain triglyceride.

Mixing of Ingredients.

1. Mix the medium-chain triglyceride, for example, Akomed R (Karlshamns AB, Karlshamn Sweden), and sunflower oil, for example, Akosun (Karlshamns AB, Karlshamn Sweden), with silicon dioxide (Cab-o-sil M5P, M5P, Cabot) in a Bolz mixing machine/tank (Alfred BOLZ Apparatebau GmbH, Wangen im Allgäu, Germany).

2. Homogenization. A Sine pump and dispax (Sine Pump, Arvada, Colorado) are connected to the Bolz mixer and the mixture is homogenized.

3. Vacuum-drying. The mixture is dried under 10 mBar vacuum in the Bolz tank for 12 hours.

4. Adding *Lactobacillus* bacteria. About 20 kg of dried oil mixture is moved to a 50 liter stainless steel vessel. *Lactobacillus* bacteria powder, preferably freeze-dried; the amount of *Lactobacillus* bacteria used would vary depending on the amount wanted in the oil, but one example would be to add 0.2 kg of culture having $10^{11}$ CFU per g, is added. It is mixed slowly until homogenous.

5. Mixing. The premix with *Lactobacillus* bacteria is brought back to the Bolz mixer.

6. Discharging. The suspension is discharged to a 200-liter glass vessel and covered with nitrogen. The suspension is held in the vessel until filling in spray bottles to be used for oral administration to a human for the prevention or treatment of serotonin deficiency.

Example 8—Manufacture of a Probiotic Product in a Tablet Format for Use in Serotonin Deficiency In this example, *Lactobacillus* strain capable of producing serotonin under aerobic conditions is used to manufacture a tablet for use in the prevention, inhibition and/or treatment of serotonin deficiency in humans. The *Lactobacillus* strain is grown and lyophilized, using standard methods for growing lactobacilli in the industry.

The following steps illustrate an example of a manufacturing process for tablets containing the selected bacterial strain, including glucose encapsulation. It is understood that excipients, fillers, flavors, encapsulators, lubricants, anticaking agents, sweeteners and other components of tablet products as are known in the art, may be used without affecting the efficacy of the product:

1. Melting. Melt SOFTISAN™ 154 (SASOL GMBH, Bad Homburg, Germany) in a vessel and heat it to 70° C. to assure complete disruption of the crystalline structure. Then cool it down to 52-55° C. (just above its hardening point).

2. Granulation. Transfer *Lactobacillus* bacteria freeze-dried powder to a Diosna high-shear mixer/granulator, or equivalent. Add slowly during approximately 1 minute the melted SOFTISAN™ 154 to the *Lactobacillus* bacteria powder. Use chopper during the addition.

3. Wet-sieving. Immediately after the granulation, pass the granules through a 1 mm sieving net by using a Tornado mill. The sieved granulate is packed in alu-pouches, made out of PVC-coated aluminum foil, sealed with a heat sealer to form a pouch, together with desiccant pouch, and stored refrigerated until mixing. The granulated batch is divided for two tablet batches.

4. Add encapsulated D-glucose (G8270, >99.5% glucose, Sigma), encapsulated using standard microencapsulating methods as known in the art. The amount of sugar is dependent on the total CFU of the added powder of dry *Lactobacillus* bacteria, a standard level can be 1 gram of sugar per total CFU of $10^8$ of bacteria but this could also be varied down to 0.1 gram or 0.01 gram up to 10 gram even up to 100 gram of sugar.

5. Mixing. Mix all the ingredients in a mixer, to a homogenous blend.

6. Compression. Transfer the final blend to the hopper of a rotary tablet press and compress tablets with a total weight of 765 mg, in a Kilian compressor.

7. Bulk packaging. The tablets are packed in alu-pouches together with a drying pouch of molecular sieve. The alu-pouch is put in a plastic bucket and stored in a cool place at least one week, before final package. The use of SOFTISAN™, a hydrogenated palm oil, enables the *Lactobacillus* cells to be encapsulated in fat and environmentally protected.

As stated above, the product of the embodiments may be in forms other than tablet, and standard methods of preparing the underling underlying product as are known in the art are beneficially used to prepare the product of the invention including the selected *Lactobacillus* culture.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible. The scope of the present invention is, however, defined by the appended claims.

The invention claimed is:

1. A *Lactobacillus reuteri* strain selected from the group consisting of *L. reuteri* strain DSM 33509, *L. reuteri* strain DSM 33632, *L. reuteri* strain DSM 33633, *L. reuteri* strain DSM 33634, and *L. reuteri* strain DSM 33635.

2. A *Lactobacillus reuteri* strain selected from the group consisting of *L. reuteri* strain DSM 33509, *L. reuteri* strain DSM 33632, *L. reuteri* strain DSM 33633, *L. reuteri* strain DSM 33634, and *L. reuteri* strain DSM 33635 in a dried, frozen or lyophilized form.

3. The *Lactobacillus reuteri* strain of claim 1, wherein the *L. reuteri* strain is DSM 33509.

4. The *Lactobacillus reuteri* strain of claim 1, wherein the *L. reuteri* strain is DSM 33632.

5. The *Lactobacillus reuteri* strain of claim 1, wherein the *L. reuteri* strain is DSM 33633.

6. The *Lactobacillus reuteri* strain of claim 1, wherein the *L. reuteri* strain is DSM 33634.

7. The *Lactobacillus reuteri* strain of claim 1, wherein the *L. reuteri* strain is DSM 33635.

8. The *Lactobacillus reuteri* strain of claim 2, wherein the *L. reuteri* strain is DSM 33509.

9. The *Lactobacillus reuteri* strain of claim 2, wherein the *L. reuteri* strain is DSM 33632.

10. The *Lactobacillus reuteri* strain of claim 2, wherein the *L. reuteri* strain is DSM 33633.

11. The *Lactobacillus reuteri* strain of claim 2, wherein the *L. reuteri* strain is DSM 33634.

12. The *Lactobacillus reuteri* strain of claim 2, wherein the *L. reuteri* strain is DSM 33635.

13. A method for treating a serotonin deficiency and/or a disease related to serotonin deficiency in a subject in need thereof, the method comprising administering to the subject a *Lactobacillus reuteri* bacterial strain selected from the group consisting of *L. reuteri* DSM 33509, *L. reuteri* DSM 33632, *L. reuteri* DSM 33633, *L. reuteri* DSM 33634, and *L. reuteri* DSM 33635.

14. The method of claim 13, wherein the *L. reuteri* strain strain is capable of attaching to intestinal mucus and/or capable of adhering to the gastrointestinal mucosa and capable of producing and extracellularly releasing serotonin under aerobic conditions on the intestinal mucosae of the subject.

15. The method of claim 13, wherein the disease related to serotonin deficiency is selected from the group consisting of a cardiovascular disease and APECED.

16. The method of claim 13, wherein the disease related to serotonin deficiency is selected from a group of disorders or diseases of the central nervous system, consisting of anxiety, depressed mood, aggression, poor memory, eating disorders, obsessive-compulsive disorder, panic disorder, post-traumatic stress disorder, and social anxiety disorder.

17. The method of claim 13, wherein the disease related to serotonin deficiency is selected from a group of disorders or diseases of the gastrointestinal system, consisting of a gastrointestinal motility disorder, IBS or IBD.

18. The method of claim 13, wherein the disease related to serotonin deficiency is selected from osteoporosis, osteopenia, and bone loss conditions, including glucocorticoid-associated bone loss.

* * * * *

UNITED STATES PATENT AND TRADEMARK OFFICE
CERTIFICATE OF CORRECTION

PATENT NO. : 12,295,975 B2
APPLICATION NO. : 17/623543
DATED : May 13, 2025
INVENTOR(S) : Grasset et al.

It is certified that error appears in the above-identified patent and that said Letters Patent is hereby corrected as shown below:

In the Specification

Column 1, Line 56: Please correct "(MDC)" to read --(AADC)--

Column 3, Line 15: Please insert a paragraph break between "sample." and "Another"

Column 14, Line 31: Please insert a paragraph break between "sample." and "Hence,"

Column 14, Lines 44-45: Please insert a paragraph break between "bacteria." and "A body"

Column 18, Line 38: Please correct "MUCUS" to read --mucus--

Column 21, Line 67: Please insert a paragraph break between "CFUs." and "The lactic"

Column 23, Line 59: Please correct "$Na_2S.9H_2O$" to read --$Na_2S \cdot 9H_2O$--

Column 28, Line 46: Please correct "$Na_2S.9H_2O$" to read --$Na_2S \cdot 9H_2O$--

Column 34, Line 22: Please correct "EDTA.4Na" to read --EDTA•4Na--

Column 34, Line 48: Please correct "strain DSM 33662)" to read --strain (DSM 33662)--

In the Claims

Column 37, Lines 10-11, Claim 14: Please correct "*L. reuteri* strain strain is" to read --*L. reuteri* strain is--

Signed and Sealed this
Seventh Day of October, 2025

John A. Squires
*Director of the United States Patent and Trademark Office*